(12) United States Patent
Safar et al.

(10) Patent No.: US 7,223,763 B2
(45) Date of Patent: May 29, 2007

(54) SUBSTITUTED SULFONAMIDES AND UREAS USEFUL FOR INHIBITING KINASE ACTIVITY

(75) Inventors: Pavel Safar, Tucson, AZ (US); Armin Walser, Tucson, AZ (US); Stephen James Shimshock, Hillsborough, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 489 days.

(21) Appl. No.: 10/835,630

(22) Filed: Apr. 30, 2004

(65) Prior Publication Data
US 2004/0204582 A1   Oct. 14, 2004

Related U.S. Application Data

(62) Division of application No. 10/191,718, filed on Jul. 9, 2002, now Pat. No. 6,777,577.

(60) Provisional application No. 60/304,020, filed on Jul. 9, 2001.

(51) Int. Cl.
*A61K 31/496* (2006.01)
*A61K 31/4545* (2006.01)
*C07D 241/04* (2006.01)
*C07D 401/04* (2006.01)
*C07D 211/06* (2006.01)

(52) U.S. Cl. ............... 514/252.12; 514/317; 544/358; 546/207; 546/229

(58) Field of Classification Search ........... 544/358; 546/207, 229; 514/252.12, 317
See application file for complete search history.

(56) References Cited

U.S. PATENT DOCUMENTS 6,362,210 B1 *   3/2002   Hauel et al. .............. 514/396
6,500,803 B1   12/2002   Klingler et al.
6,727,250 B2 *   4/2004   Hauel et al. .............. 514/239.5

FOREIGN PATENT DOCUMENTS

WO     WO 00/49018      8/2000

OTHER PUBLICATIONS

B. Lawrence Riggs, Overview of Osteoporosis, West Journal Medicine (1991, pp. 63-77, vol. 154).
Fahad A. Al-Obeidi et al., Protein Tyrosine Kinases: Structure, Substrate Specificity, and Drug Discovery, Biopolymer Peptide Science (1998, pp. 197-223, vol. 47).
W. A. Peck, et al, Consensus Development Conference: Diagnosis, Prophylaxis, and Treatment of Osteoporosis, The American Journal of Medicine (1993, pp. 646-650, vol. 94).

* cited by examiner

*Primary Examiner*—Kamal A. Saeed
*Assistant Examiner*—Janet L. Coppins
(74) *Attorney, Agent, or Firm*—Balaram Gupta

(57) ABSTRACT

Sulfonamide and urea compounds having an inhibitory effect on Src kinase including enantiomers, stereoisomers and tautomers thereof, as well as pharmaceutically acceptable salts or solvates of said compound, said compound having the general structure shown in Formula II are disclosed and claimed:

Formula II

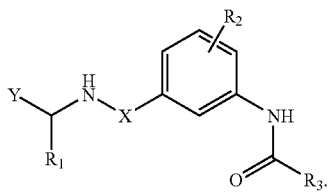

16 Claims, No Drawings

SUBSTITUTED SULFONAMIDES AND UREAS USEFUL FOR INHIBITING KINASE ACTIVITY

This application is a division of U.S. application Ser. No. 10/191,718, filed Jul. 9, 2002 now U.S. Pat. No. 6,777,577, now allowed, which claims the benefit of U.S. Provisional Application No. 60/304,020, filed Jul. 9, 2001.

FIELD OF THE INVENTION

The present invention discloses novel substituted amide compounds, specifically sulfonamides, and urea compounds having enzyme inhibiting properties, especially for inhibiting protein tyrosine kinases.

BACKGROUND OF THE INVENTION

The novel compounds of the present invention may have general therapeutic value for the treatment of such diseases as cancer, including bone, colon or breast cancer; immunodeficiency disorders and diabetes; atherosclerosis, osteoporosis, leukemia and other conditions such as coronary heart disease, congestive heart failure, renal failure and diseases of the central nervous system where the compounds exert a beneficial effect. The inventive compounds have been found to inhibit the Src protein tyrosine kinase, a member of the Src family.

The Src family consists of nine members—Src. Yes, Fgr, Yrk. Fyn. Lyn, Hck, Lck and Blk—which share the same domain structure. The N-terminal, unique domain contains a myristylation site and frequently a palmitoylation site. It is followed by the regulatory SH3 and SH2 domains, a catalytic domain that is bilobal and has its active site wedged between the two lobes, and a C-terminal regulatory tail that contains the hallmark regulatory tyrosine residue (Tyr527 in Src). Kinase activity is reduced when the latter is phosphorylated and bound to the SH2 domain. The SH2 and SH3 domains bind phosphotyrosyl and proline-rich peptides, respectively: through these interactions, they participate in intra- and intermolecular regulation of kinase activity, as well as localization and substrate recognition.

There is a wealth of evidence that tyrosine phosphorylation plays a crucial role in many cell regulatory processes. Fahad Al-Obeidi et al., *Biopolymers* (Peptide Science) 47, 197–223 (1998). Researchers have found that functional perturbation of the kinases results in many diseases. Thus, there has been a great deal of effort applied in attempts to develop potent and selective inhibitors for these enzymes.

The Src protein tyrosine kinase plays a role in osteoporosis and other bone diseases. Osteoporosis is defined as a systemic skeletal disease which is characterized by low bone mass and microarchitectural deterioration of bone tissue resulting in an increase in bone fragility and susceptibility to fracture, W. A. Peck, et al., *Am. J. Med.,* 94, 646, (1993) Conference Report. It is estimated that osteoporosis causes 1.5 million fractures annually with a total medical cost of $13.8 billion. National Osteoporosis Foundation, August, 1997. The most typical sites of such fractures are the hip, spine, wrist, and ribs. It is also estimated that one out of every two women and one in eight men will have an osteoporosis related fracture in their lifetime. Osteoporosis is most commonly associated with postmenopause and age-related bone tissue loss. In addition, osteoporosis can occur secondarily to various drugs and diseases such as corticosteroids, anticonvulsants, alcohol, malabsorption syndromes, primary biliary cirrhosis, myeloma, thalassemia, thyrtoxicosis, Cushing's syndrome, Turner's syndrome, and primary hyperparathyroidism. Drugs used in the treatment of osteoporosis are generally classified as antiresorptive or formation stimulating. In normal bone tissue, there is a balance between bone formation by osteoblasts and bone resorption by osteoclasts. When the balance of this ongoing process is upset, bone resorption can exceed bone formation resulting in quantitative bone loss. Most of the treatments have involved those that act through inhibition of bone resorption, such as calcium supplements, estrogen, calcitonin, and vitamin D, L. Riggs, *West. J. Med.,* 154, 63 (1991).

Examples of treatments which act though stimulation of bone formation are sodium fluoride, low intermittent dosage of parathyroid hormone, M. Missbach, et al., *Rech. Chimie Med.,* July, 1997, London.

Several reports have disclosed compelling evidence that the protein tyrosine kinase (PTK)p60c-Src (sometimes referred to as c-Src) plays a critical role in osteoclastic function, M. Missbach, et al., ibid. It was reported that, in vitro, kinase inhibitors of c-Src are capable of reducing osteoclastic bone resorption, Ibid. Osteoclasts are bone marrow cells that are responsible for breaking down or remodeling bone. Once an osteoclast comes into contact with the bone surface, it adheres tightly to the bone, flattens out, and begins the process of secreting materials which results in dissolution of the bone. This fundamental action of osteoclasts is dependent on Src kinase. In this case it is clear that at least one of the roles for Src kinase is in the regulation of cytoskeletal changes involved in establishing the close bone cell interface and in polarizing cellular secretion toward the bone surface. Thus, animals genetically engineered to lack Src kinase show abnormalities that indicate a general inability to resorb bone.

In addition, osteoclasts derived from these animals are unable the to flatten on bone, nor are they able to dissolve it. Consistent with these results, small molecule inhibitors of Src kinase have been shown to be useful in countering bone loss in animal models of osteoporosis, such as IL-1-induced hypercalcemia, and bone loss in ovariectomized rats. Src kinase inhibitors would be useful for the treatment of disorders marked by inappropriate bone resorption like osteoporosis.

SUMMARY OF THE INVENTION

The present invention provides novel sulfonamides and ureas having inhibitory activity against osteoporosis and related bone tissue loss. The inventive compounds have the general structure shown in Formula II, including enantiomers, stereoisomers and tautomers thereof, as well as its pharmaceutically acceptable salts or solvates:

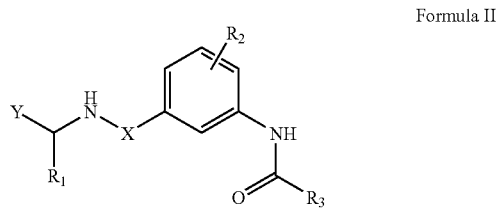

Formula II wherein $R_1$ is selected from the group consisting of H, straight chain $C_1$–$C_6$ alkyl; branched $C_1$–$C_6$ alkyl; —$(CH_2)_p$—$Ar_1$; and —$(CH_2)_p$—$R_4$, wherein p is 1 or 2;

Ar$_1$ is phenyl or naphthyl optionally substituted with a straight chain or branched C$_1$–C$_6$ alkyl group; and R$_4$ is C$_5$–C$_7$ cycloalkyl;

R$_2$ is selected from the group consisting of:

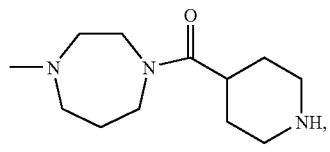

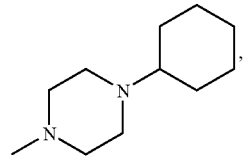

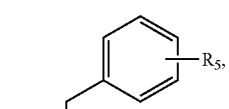

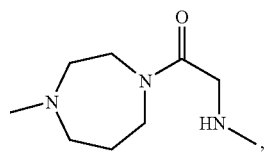

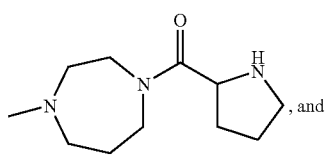

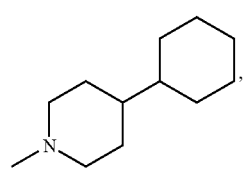

R$_5$ is selected from the group consisting of H, straight chain C$_1$–C$_6$ alkyl; branched C$_1$–C$_6$ alkyl;

R$_3$ is —(CH$_2$)$_q$—Ar$_2$ or —(CH=CH)-Phenyl, wherein q is an integer from 0 to 4; and Ar$_2$ is selected from the group consisting of:

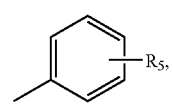

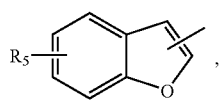

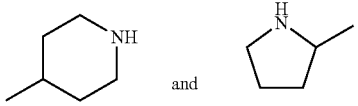

X is:

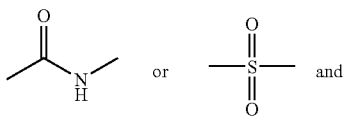

Y is selected from the group consisting of:

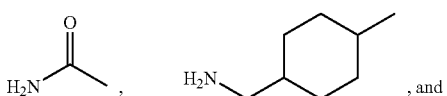

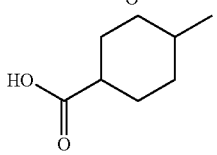

with the proviso that when Y is any of the moieties:

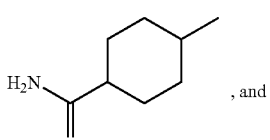

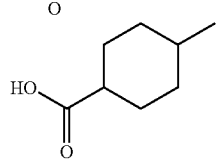

then R$_1$ is H.

When used herein, unless otherwise defined, the following terms have the given meanings:

alkyl (including the alkyl portions of lower alkoxy)—represents a straight or branched, saturated hydrocarbon chain having from 1 to 10 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted.

The term "pharmaceutically acceptable salt" is a non-toxic organic or inorganic acid addition salt of the base compounds represented by Formulas I and II.

Included within the scope of the present invention are the individual stereoisomers, diastereomers and geometric isomers of formula (1) and (II), and enantiomers thereof. The term "stereoisomers" is a general term for all isomers of individual molecules that differ only in the orientation of their atoms in space. It includes geometric (cis/trans) isomers, and isomers of compounds with more than one chiral center that are not mirror images of one another (diastereomers). The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction. The term "racemic mixture" or "racemic modification" refers to a mixture of equal parts of enantiomers and which is optically inactive. As used herein the prefixes "(+)" and "(−)" are employed to designate the sign of rotation of the plane of polarized light by the compound, with (+) meaning the compound is dextrorotatory and (−) meaning the compound is levorotatory. For amino-acids, the designations L/D, or R/S can be used as described in IUPAC-IUB Joint Commission on Biochemical Nomenclature, *Eur. J. Biochem.* 138, 9–37 (1984).

A further feature of the invention is pharmaceutical compositions containing as active ingredient a compound of Formula I (or its salt, solvate or isomers) or Formula II (or its salt, solvate or isomers) together with a pharmaceutically acceptable carrier or excipient.

The invention also provides methods for administering to a patient suffering from one or more of the aforesaid diseases a therapeutically effective inhibitory amount of a compound of Formula I or Formula II, or pharmaceutical compositions comprising a compound of Formula I or Formula II.

DETAILED DESCRIPTION OF THE INVENTION

In one embodiment, the present invention provides novel compounds of Formula I or Formula II shown above, where the various symbols are as defined. Representative amide compounds of the invention which exhibit excellent Src kinase inhibitory activity belonging to Formula I are listed below by names and structure.

Names and Structural Formulas

1. N-[4-Amidinobenzoyl]-N-[3-phenoxybenzyl]-3-(4-biphenyl)-alanyl-glycyl-amide
    IUPAC Name:
    ALPHA-[[4-(AMINOIMINOMETHYL)BENZOYL][(3-PHENOXYPHENYL)METHYL]AMINO]-N-(2-AMINO-2-OXOETHYL)-1,1'-BIPHENYL-4-PROPANAMIDE Structure:

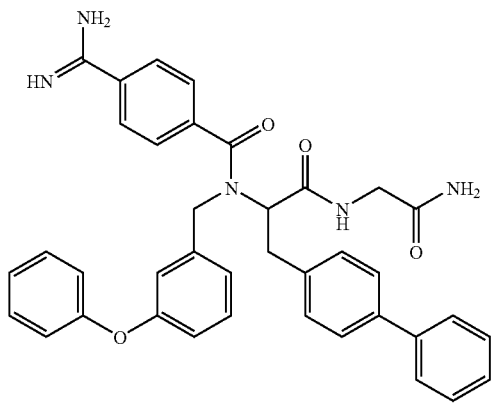

2. N-[3-Amidinobenzoyl]-N-[3-(4-tert-butylphenoxy)benzyl]-cyclohexylalanyl-glycyl-amide
    IUPAC Name:
    3-(AMINOIMINOMETHYL)-N-[1-[[(2-AMINO-2-OXOETHYL)AMINO]CARBONYL]-2-CYCLOHEXYL-ETHYL]-N-[[3-[4-(1,1-DIMETHYLETHYL)PHENOXY]PHENYL]METHYL]BENZAMIDE Structure:

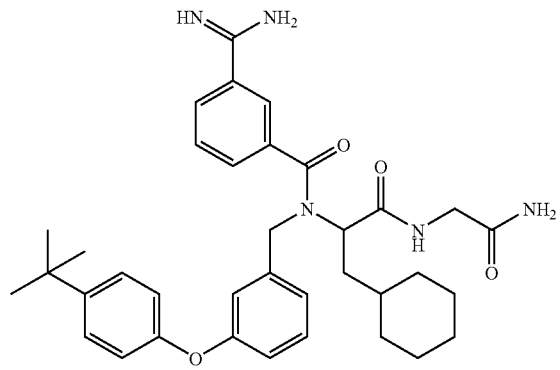

3. N-[3-Amidinobenzoyl]-N-[3-(4-tert-butylphenoxy)benzyl]-4-aminophenylalanyl-glycyl-amide IUPAC Name:
4-AMINO-ALPHA-[[3-(AMINOIMINOMETHYL)BENZOYL][[3-[4-(1,1-DIMETHYLETHYL)PHENOXY]PHENYL]METHYL]AMINO]-N-(2-AMINO-2-OXOETHYL)BENZENEPROPANAMIDE Structure:

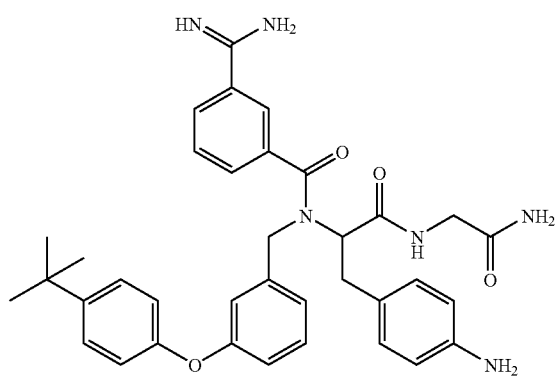

4. N-[3-Amidinobenzoyl]-N-[3-(4-tert-butylphenoxy)benzyl]-1-naphthylalanyl-glycyl-amide IUPAC Name:
4-AMINO-ALPHA-[[3-(AMINOIMINOMETHYL)BENZOYL][[3-[4-(1,1-DIMETHYLETHYL)PHENOXY]PHENYL]METHYL]AMINO]-N-(2-AMINO-2-OXOETHYL)-1-NAPHTHALENEPROPANAMIDE Structure:

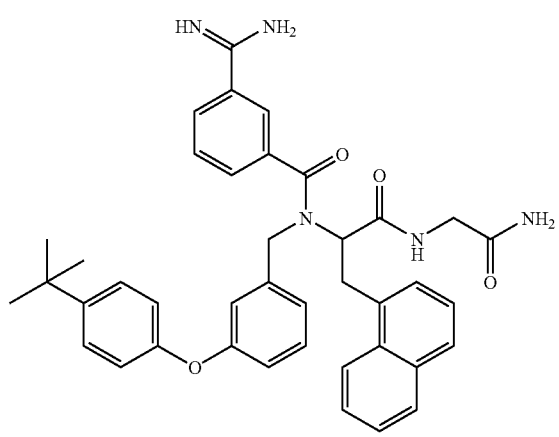

5. N-[3-Amidinobenzoyl]-N-[3-(4-tert-butylphenoxy)benzyl]-arginyl-glycyl-amide

IUPAC Name
3-(AMINOIMINOMETHYL)-N-[4-[(AMINOIMINOMETHYL) AMINO]-1-[[(2-AMINO-2-OXOETHYL) AMINO]CARBONYL]BUTYL]-N-[[3-[4-(1,1-DIMETHYLETHYL)PHENOXY]PHENYL]METHYL]BENZAMIDE Structure:

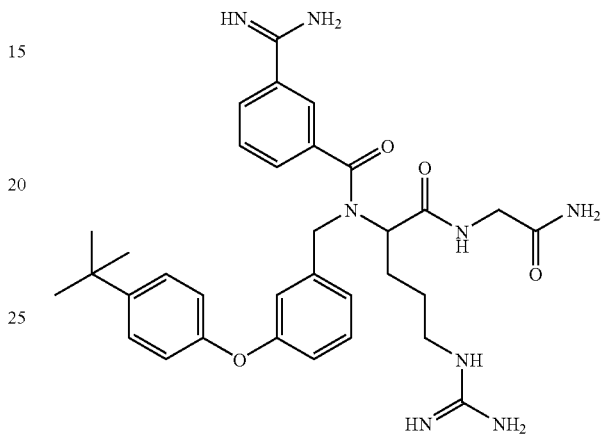

6. N-[4-Amidinobenzoyl]-N-[3-(4-tert-butylphenoxy)benzyl]-tryptanyl-glycyl-amide IUPAC Name:
4-AMINO-ALPHA-[[4-(AMINOIMINOMETHYL)BENZOYL][[3-[4-(1,1-DIMETHYLETHYL)PHENOXY]PHENYL]METHYL]AMINO]-N-(2-AMINO-2-OXOETHYL)1H-INDOLE-3-PROPANAMIDE Structure:

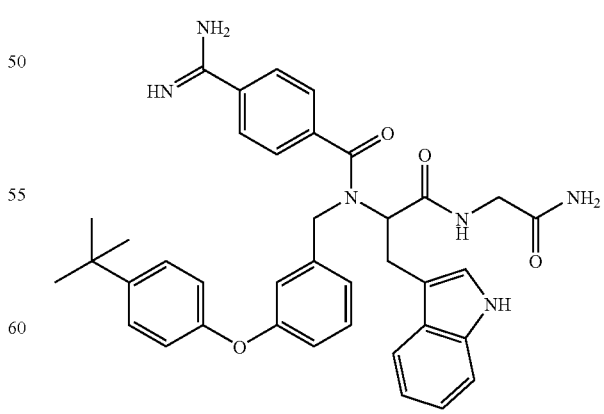

7. N-[4-Amidinobenzoyl]-N-[4-biphenylmethyl]-3-(4-biphenyl)alanyl-glycyl-amide

IUPAC Name:
ALPHA-[[4-(AMINOIMINOMETHYL)BENZOYL][[[1,1'-BIPHENYL]-4-YL]METHYL]AMINO]-N-(2-AMINO-2-OXOETHYL)-1,1'BIPHENYL-4-PROPANAMIDE Structure:

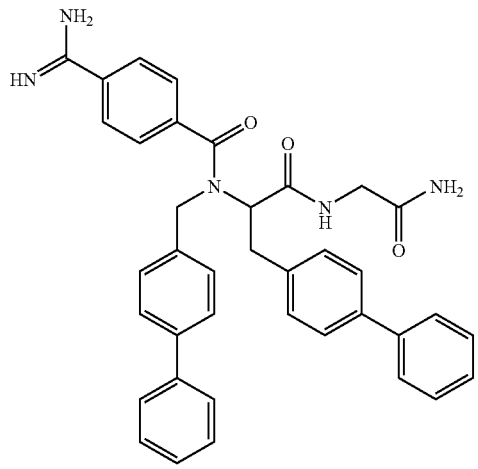

Representative urea compounds of Formula II of the invention which exhibit excellent Src kinase inhibitory activity are listed below by names and structure.

8. 4-Cyclohexyl-1-[[2-(4-phenylbutanoyl)amino]-4-[1-aminocarbonyl-2-(2-naphthyl)ethylamino]carbonylaminophenyl]piperazine
IUPAC Name:
ALPHA-[[[[4-(4-CYCLOHEXYL-1-PIPERAZINYL)-3-[(1-OXO-4-PHENYLBUTYL)AMINO]PHENYL]AMINO]CARBONYL]AMINO]-2-NAPHTHALENEPROPANAMIDE Structure:

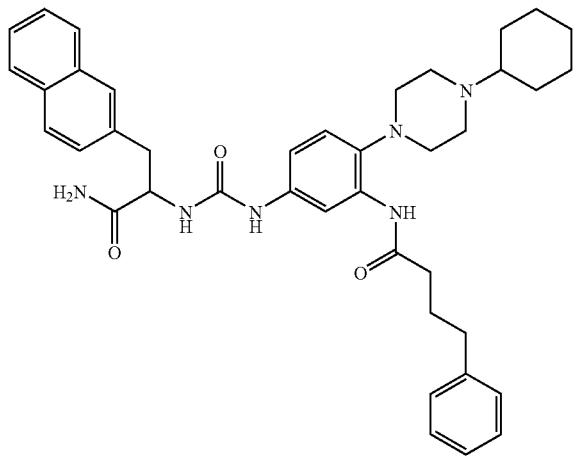

9. 4-Cyclohexyl-1-[[2-cinnamoylamino]-4-[1-aminocarbonyl-2-(2-naphthyl)ethylamino]carbonylaminophenyl]piperazine
IUPAC Name:
ALPHA-[[[[4-(4-CYCLOHEXYL-1-PIPERAZINYL)-3-[(1-OXO-3-PHENYL-2-PROPENYL)AMINO]PHENYL]AMINO]CARBONYL]AMINO]-2-NAPHTHALENEPROPANAMIDE Structure:

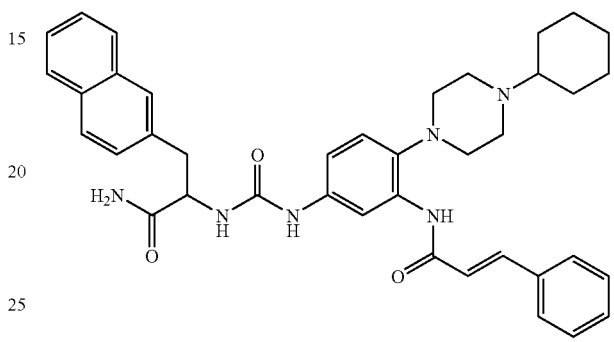

10. Common Name:
4-Cyclohexyl-1-[[2-cinnamoylamino]-4-[(1-aminocarbonyl-3-phenyl)propylamino]carbonylaminophenyl]piperazine
IUPAC Name:
ALPHA-[[[[4-(4-CYCLOHEXYL-1-PIPERAZINYL)-3-[(1-OXO-3-PHENYL-2-PROPENYL)AMINO]PHENYL]AMINO]CARBONYL]AMINO]BENZENEBUTANAMIDE Structure:

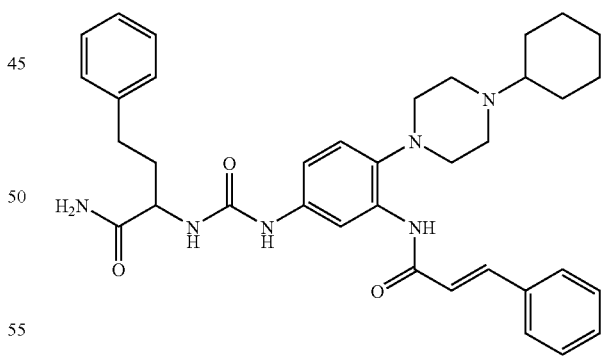

11. 4-Cyclohexyl-1-[[2-(4-phenylbutanoyl)amino]-4-[(1-aminocarbonyl-3-phenyl)propylamino]carbonylaminophenyl]piperazine
IUPAC Name
ALPHA-[[[[4-(4-CYCLOHEXYL-1-PIPERAZINYL)-3-[(1-OXO-4-PHENYLBUTL)AMINO]PHENYL]AMINO]CARBONYL]AMINO]BENZENEBUTANAMIDE Structure:

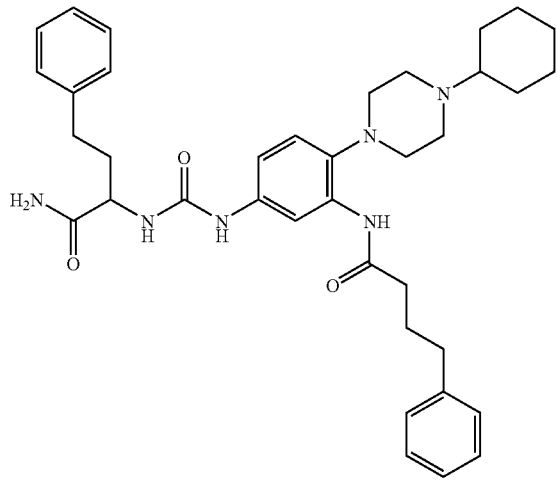

12. 4-Cyclohexyl-1-[[2-cinnamoylamino]-4-[(1-aminocarbonyl-2-cyclohexylethylamino)carbonylaminophenyl]piperazine
   IUPAC Name:
   2-[ALPHA-[[[[4-(4-CYCLOHEXYL-1-PIPERAZINYL)-3-[(1-OXO-3-PHENYL-2-PROPENYL)AMINO]PHENYL]AMINO]-CARBONYL]AMINO]]3-(CYCLOHEXYL)PROPANAMIDE Structure:

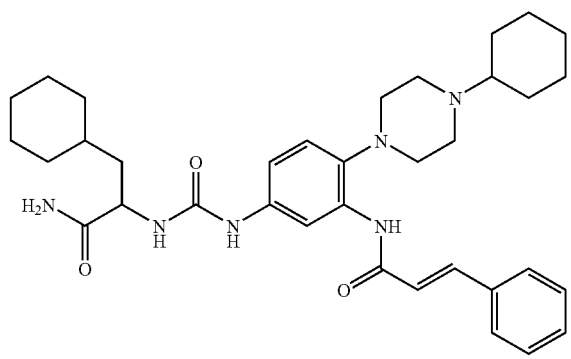

13. 4-(Piperidin-4-yl)carbonyl-1-[[2-(4-phenylbutanoyl)amino]-4-[1-aminocarbonyl-2-(2-naphthyl)ethylamino]-carbonylaminophenyl]homopiperazine
   IUPAC Name:
   2-[ALPHA-[[[[4-[HEXAHYDRO-4-(4-PIPERIDINYLCARBONYL)-1H-1,4-DIAZEPIN-1-YL]-3-[(1-OXO-5-PHENYLPENTYL)AMINO]PHENYL]AMINO]CARBONYL]AMINO]]-3-[NAPHTH-2-YL]PROPANAMIDE Structure:

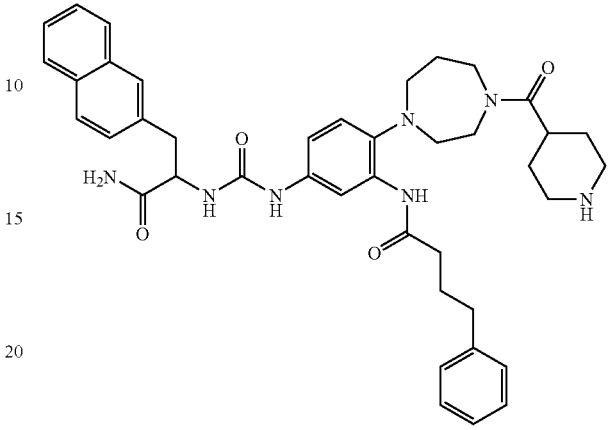

14. 4-(Piperidin-4-yl)carbonyl-1-[[2-(2-benzofuranoyl)amino]-2-(2-naphthyl)ethylamino]carbonylaminophenyl]homopiperazine
   IUPAC Name:
   2-[ALPHA-[[[[4-[HEXAHYDRO-4-(4-PIPERIDINYLCARBONYL)-1H-1,4-DIAZEPIN-1-YL]-3-[(1-OXO-1-BENZOFURAN-2-YL)AMINO]PHENYL]AMINO]CARBONYL]AMINO]]-3-(NAPHTH-2-YL)-PROPANAMIDE Structure:

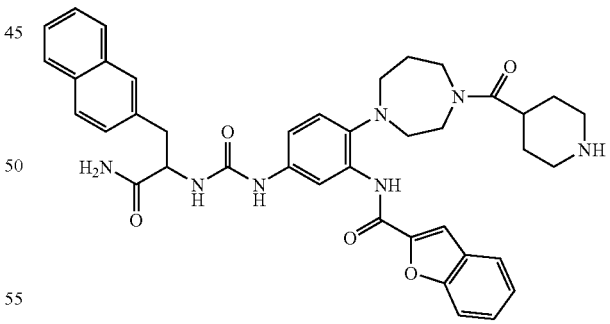

15. 4-(Piperidin-4-yl)carbonyl-1-[[2-(2-benzofuranoyl)amino]-4-[1-aminocarbonyl-2-cyclohexylethylamino]carbonylamino phenyl]homopiperazine
   IUPAC Name:
   2-[ALPHA-[[[[4-[HEXAHYDRO-4-(4-PIPERIDINYLCARBONYL)-1H-1,4-DIAZEPIN-1-YL]-3-[(1-OXO-1-

BENZOFURAN-2-YL)AMINO]PHENYL]AMINO]
CARBONYL]AMINO]]-3-CYCLOHEXYL-
PROPANAMIDE

Structure:

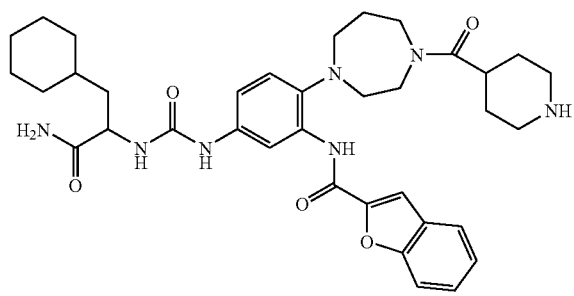

16.  4-(Piperidin-4-yl)carbonyl-1-[2-[(2-benzofuranoyl)
amino]-4-[[(4-aminocarbonyl)cyclohexylmethylamino]car-
bonylaminophenyl]homopiperazine
 IUPAC Name:
4-[ALPHA-[4-[[[[4-[HEXAHYDRO-4-(4-PIPERIDINYL-
 CARBONYL)-1H-1,4-DIAZEPIN-1-YL]-3-[(1-OXO-1-
 BENZOFURAN-2-YL)AMINO]PHENYL]AMINO]
 CARBONYL]AMINO]METHYL]]-CYCLOHEX-1-
 YLFORMAMIDE Structure:

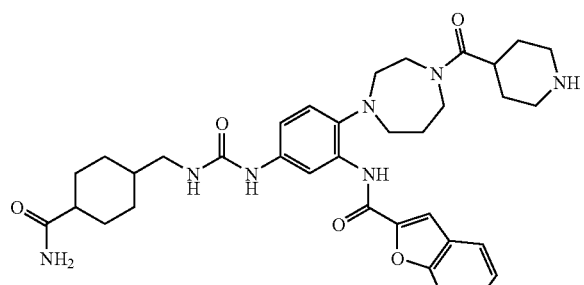

17. 4-(Methylaminomethyl)carbonyl-1-[2-[(2-benzo-fura-
noyl)amino]-4-[[(4-aminocarbonyl)cyclohexylmethy-
lamino]carbonylaminophenyl]homopiperazine
 IUPAC Name:
4-[ALPHA-[4-[[[[4-[HEXAHYDRO-4-[[[METHYL]
 AMINO]METHYL]CARBONYL)-1H-1,4-DIAZEPIN-
 1-YL]-3-[(1-OXO-1-BENZOFURAN-2-YL)AMINO]

PHENYL]AMINO]CARBONYL]AMINO]METHYL]]
CYCLOHEX-1-YLFORMAMIDE

Structure:

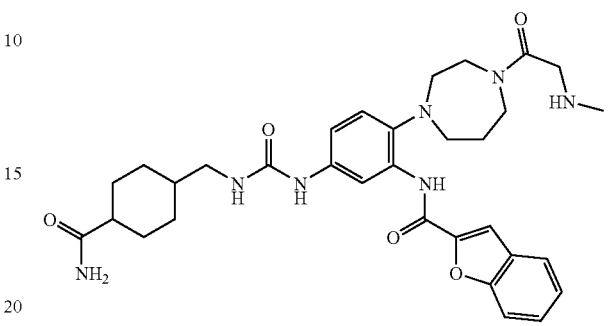

18.  4-(Pyrrolidin-2-yl)carbonyl-1-[2-[(2-benzo-furanoyl)
amino]-4-[[(4-aminocarbonyl)cyclohexyl-methyl-amino]
carbonylamino]phenyl]homopiperazine
 IUPAC Name:
4-[ALPHA-[[[[4-[HEXAHYDRO-4-(2-PYRROLIDINYL-
 CARBONYL)-1H-1,4-DIAZEPIN-1-YL]-3-[(1-OXO-1-
 BENZOFURAN-2-YL)AMINO]PHENYL]AMINO]
 CARBONYL]AMINO]METHYL]]-CYCLOHEX-1-
 YLFORMAMIDE Structure:

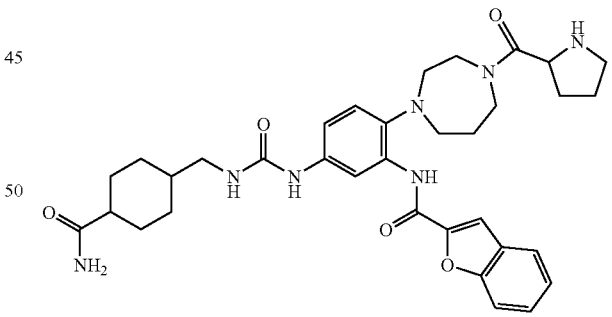

19.  4-(Piperidin-1-yl)-1-[2-[(2-benzofuranoyl)amino]-4-
[[(4-aminocarbonyl)cyclohexylmethylamino]carbonylami-
nophenyl]piperidine
 IUPAC Name:
4-[ALPHA-[4-[[[[4-[4-(PIPERIDIN-1-YL)-1-PIPERIDI-
 NYL]-3-[(1-OXO-1-BENZOFURAN-2-YL)AMINO]

PHENYL]AMINO]CARBONYL]AMINO]METHYL]]-CYCLOHEX-1-YLFORMAMIDE

Structure:

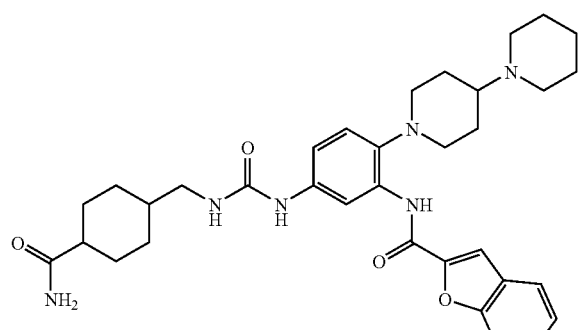

20. 4-(Piperidin-4-yl)carbonyl-1-[[2-(4-phenylbutanoyl)amino]-4-[1-aminocarbonyl-2-cyclohexylethylamino]carbonylaminophenyl]homopiperazine IUPAC Name:
N-[5-[[[[1-(CARBOXY)-1-(CYCLOHEXYL-METHYL)]AMINO]-CARBONYL]AMINO]-2-[HEXAHYDRO-4-(4-PIPERIDINYL-CARBONYL)-1H-1,4-DIAZEPIN-1-YL]PHENYL]BENZENE-BUTANAMIDE Structure:

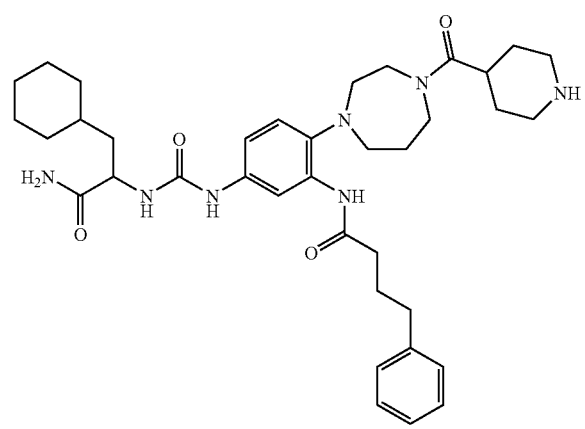

21. 4-(Piperidin-4-yl)carbonyl-1-[[2-(4-phenylbutanoyl)amino]-4-[(1-aminocarbonyl-2-(naphth-2-yl))ethylamino]-carbonylaminophenyl]homopiperazine IUPAC Name:
2-[ALPHA-[[[[4-[HEXAHYDRO-4-(4-PIPERIDINYL-CARBONYL)-1H-1,4-DIAZEPIN-1-YL]-3-[(1-OXO-4-PHENYL-BUTYL)AMINO]PHENYL]AMINO]CARBONYL]AMINO]]-3-(NAPHTH-2-YL)-PROPANAMIDE Structure:

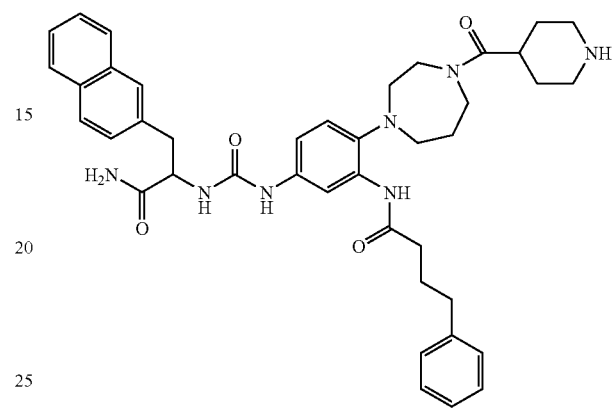

Representative sulfonamide compounds of the invention which exhibit excellent Src kinase inhibitory activity of the Formula II are listed by names and structure below.

22. N-(1-Aminocarbonyl-2-methylpropyl)-2-[(4-phenylmethyl)piperidin-1-yl]-5-[(2-pyrrolidinocarbonyl)amino]phenylsulfonamide IUPAC Name:
ALPHA-2-[[[[2-(4-BENZYL)-1-PIPERIDINYL]-5-[(PYRROLIDIN-2-YL)CARBONYLAMINO]PHENYL]SULFONYL]AMINO]-3-METHYLBUTANAMIDE Structure:

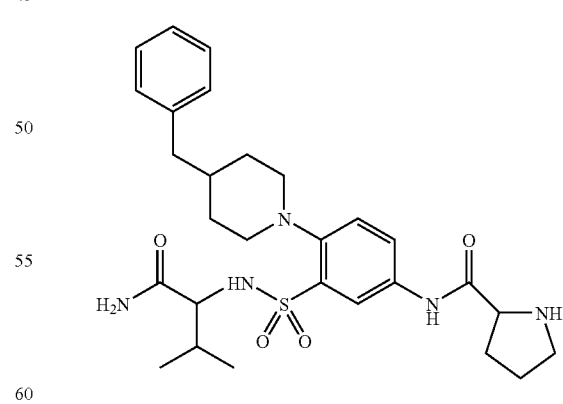

23. N-(1-Aminocarbonyl-2-methylpropyl)-2-[(4-phenylmethyl)piperidin-1-yl]-5-[(2-piperdino-carbonyl)amino]phenylsulfonamide IUPAC Name:
ALPHA-2-[[[[2-(4-BENZYL)-1-PIPERIDINYL]-5-[(PIP-
ERIDIN-4-YL)CARBONYLAMINO]PHENYL]SUL-
FONYL]AMINO]-3-METHYLBUTANAMIDE Structure:

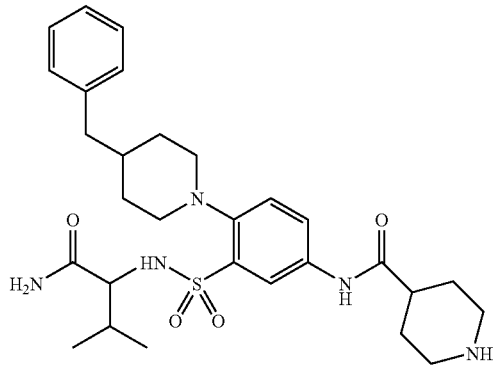

24. 1-[2-[N-(2-Aminocarbonyl-3-methylbutyl)sulfona-
mido]-5-[2-cinnamoylamino]]phenyl-4-cyclohexylpipera-
zine IUPAC Name:
ALPHA-2-[[[2-(4-CYCLOHEXYL-1-PIPERAZINYL)-5-
[(1-OXO-3-PHENYL-2-PROPENYL)CARBONY-
LAMINO]PHENYL]SULFONYL]AMINO]-3-METH-
YLBUTANAMIDE Structure:

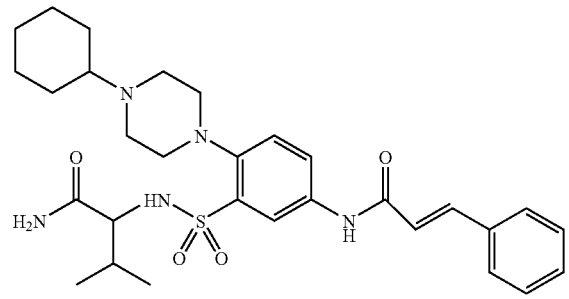

25. N-[[(4-Aminocarbonyl)cyclohexylmethyl]amino]-[2-
[(4-phenylmethyl)piperidin-1-yl]-5-[(2-pyrrolidino-carbo-
nyl)amino]phenyl]sulfonamide IUPAC Name:
4-[2-[[[[2-[(4-BENZYL)-1-PIPERIDINYL]-5-[(PYRRO-
LIDIN-2-YL)CARBONYLAMINO]PHENYL]SULFO-
NYL]AMINO]METHYL]]-CYCLOHEX-1-YLFOR-
MAMIDE Structure:

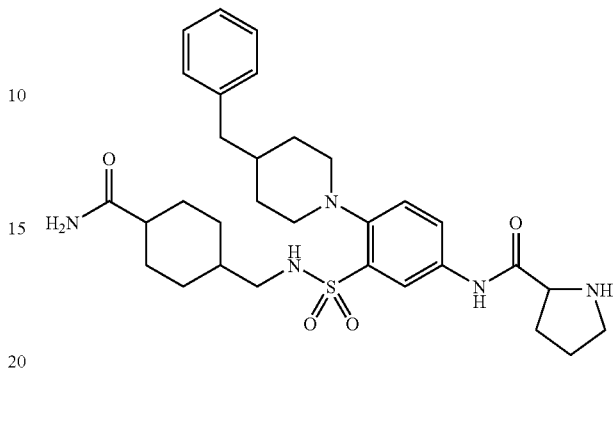

The compounds of the invention may form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, hydroxymaleic, benzoic, hydroxybenzoic, phenylacetic, cinnamic, salicyclic, 2-phenoxybenzoic, p-toluensulfonic acid, and sulfonic acids such as methane sulfonic acid and 2-hyroxyethane sulfonic acid and other mineral and carboxylic acids well known to those skilled in the art and acid metal salts such as sodium monohydrogen orthophosphate, and potassium hydrogen sulfate. Such salts can exist in either a hydrated or substantially anhydrous form. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule (e.g., compound 21 in the list above), salts may be formed with inorganic as well as organic bases such as, for example, NaOH, KOH, NH$_4$OH, tetraalkylammonium hydroxide, and the like.

As stated earlier, the invention includes tautomers, enantiomers and other stereoisomers of the compounds also. Such variations are contemplated to be within the scope of the invention.

Another embodiment of the invention discloses a method of making the substituted carboxamides, ureas and sulfonamides disclosed above. The compounds may be prepared by several processes known in the art of synthetic organic chemistry. One useful method to prepare compounds of Formula I is schematically illustrated below in connection with the compound numbered 7 above. In general, this procedure is referred to as Scheme A herein and involves: (a) bonding an amino acid to a suitably functionalized polymer support; (b) coupling another suitably substituted amino acid thereto; (c) reacting the coupled structure with an aldehyde to form a Schiff base, which is then (d) reduced to the corresponding amine; which, in turn, is converted to an amide by way of reaction with an acid chloride for example, which product may be (e) converted to the thioamide; which, in turn, is (f) methylated and (g) converted to the amidino group. The product is then cleared from the solid phase support as will be further appreciated from the following discussion.

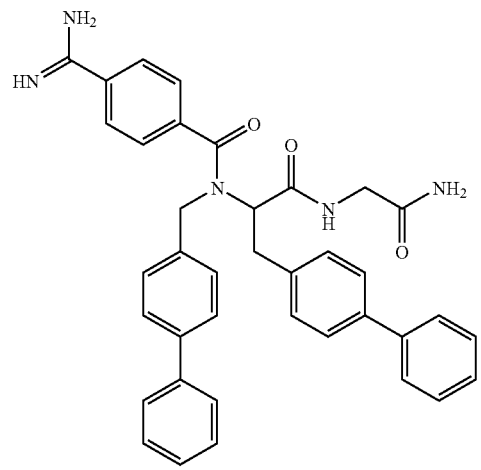

Scheme A is specifically illustrated with respect to N-[4-Amidinobenzoyl]-N-[4-biphenylmethyl]-3-(4-biphenyl)alanyl-glycyl-amide:

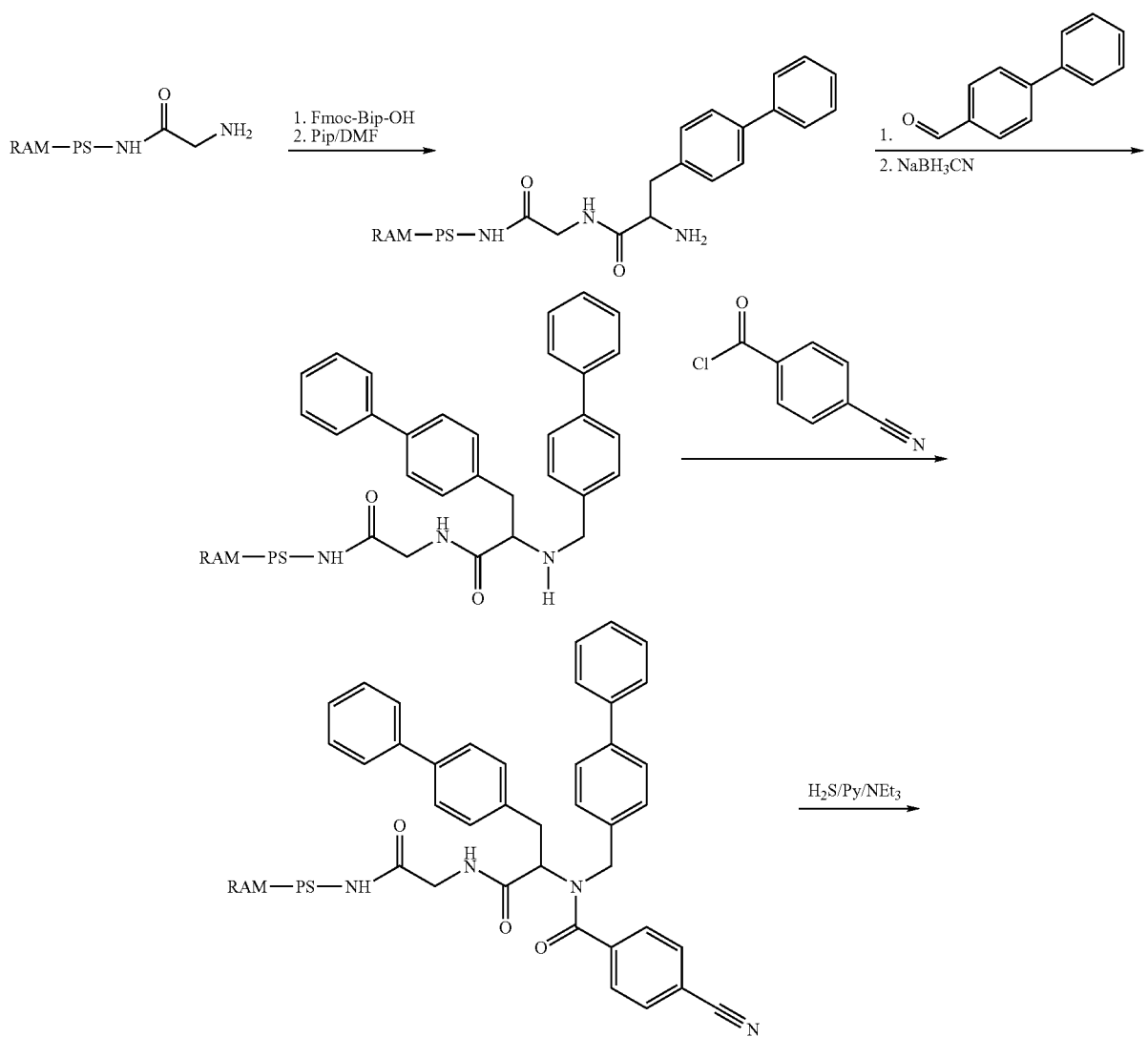

-continued
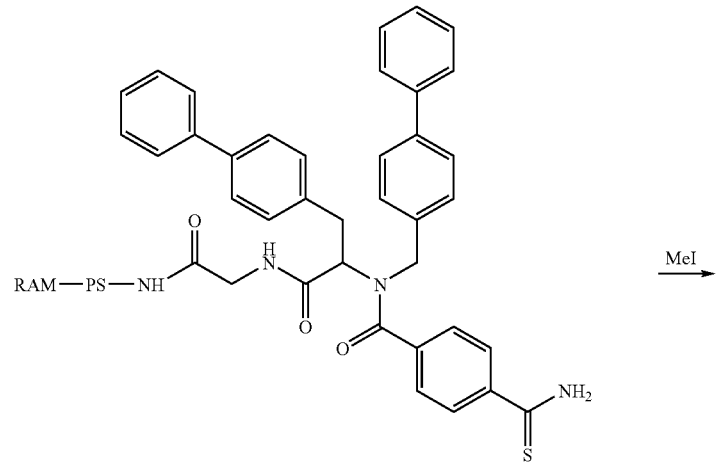
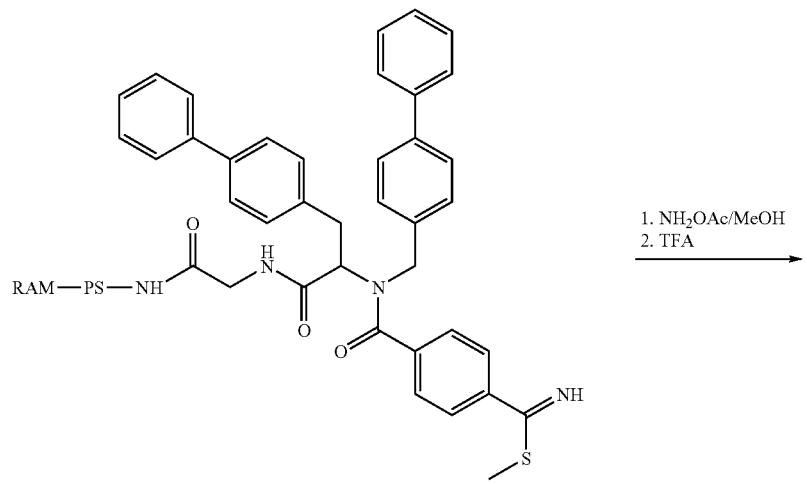
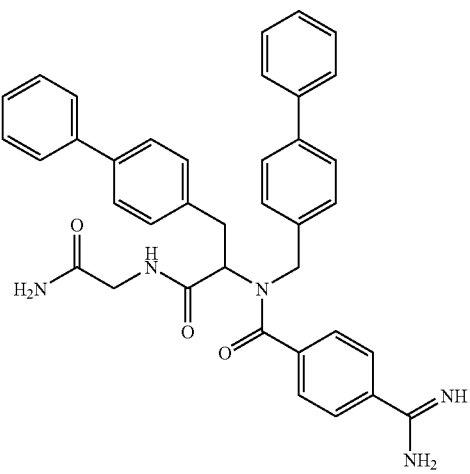
Compound 7

In Scheme A, all substituents, unless otherwise indicated, are as previously defined. The reagents and starting materials are readily available to one of ordinary skill in the art or may be prepared by conventional methods. The starting material (1) in Scheme A is an amino functionalized solid phase material, which for the purposes of synthesis was modified with linker molecule (formula III), which enables the product of the synthesis to be cleaved from the solid support (resin). Example of such linker is the Rink linker (p-[(R,S)-α-(9H-fluoren-9-yl)methoxyformamido]-2,4-dimethoxybenzyl]-phenoxyacetic acid (Bernatowicz et al., Tetrahedron Lett. 30, 4645 (1989)). Commercially available resins with the desired linker already attached can be used as well.

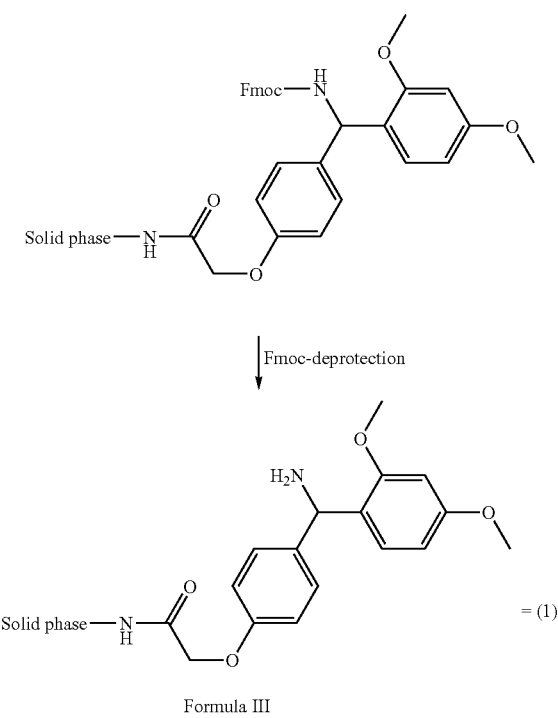

Formula III

The Rink linker attachment to a suitable solid phase is carried out by reacting an amino functionalized solid support with acid moiety of the linker molecule by standard peptide synthesis techniques well known in the art to provide an amide linkage, as shown in Example 1. Such reaction can be carried out using standard coupling procedures such as, for example, as described in Stewart and Young, *Solid Phase Peptide Synthesis*, 2$^{nd}$ ed., Pierce Chemical Co., Rockford, Ill. (1984); Gross, Meienhofer, Udenfriend, Ed., *The Peptides: Analysis, Synthesis, Biology*, Vol. 1, 2, 3, 5 and 9, Academic Press, New York, 1980–1987; Bodanszky, *Peptide Chemistry: A Practical Textbook*, Springer-Verlag, New York (1988); and Bodanszky, et al. *The Practice of Peptide Synthesis* Springer-Verlag, New York (1984), the disclosures of which are hereby incorporated by reference. If a coupling reagent (activator) is needed, suitable coupling reagent may be selected from dicyclohexylcarbodiimide (DCC), diisopropylcarbodiimide (DIC), 1-ethoxycarbonyl-2-ethoxy-1,2-dihydroquioline (EEDQ), 1-ethyl-3-(3-dimethylaminopropyl)carbodiimide hydrochloride (EDCI), n-propanephosphonic anhydride (PPA), N,N-bis(2-oxo-3-oxazolidinyl)amidophosphoryl chloride (BOP-CI), diphenylphosphoryl azide, (DPPA), Castro's reagent (BOP), 2-(1H-benzotriazol-1-yl)-1,1,3,3-tetramethyluronium salts (HBTU), 2,5-diphenyl-2,3-dihydro-3-oxo-4-hydroxythiophene dioxide (Steglich's reagent' HOTDO) and 1,1'carbonyldiimidazole (CDI). The coupling reagent may be used alone or in combination with additives such as 4-dimethylaminopyridine (DMAP), N-hydroxybenzotriazole (HOBt), N-hydroxybenzotriazine (HOOBt), N-hydroxysuccinimide) HOSu) or 2-hydroxypyridine. The coupling reactions can be performed in either solution (liquid phase) or solid phase.

As used herein, the term "solid phase support" is not limited to a specific type of support. A large number of supports are available and are known to one of ordinary skill in the art. Solid phase supports include silica gels, resins, derivatized plastic films, glass beads, cotton, plastic beads, alumina gels, polysaccharides and the like. A suitable solid phase support may be selected on the basis of desired end use and suitability for various synthetic protocols. For example, for peptide synthesis, solid phase support may refer to resins such as p-methylbenzhydrylamine (pMBHA) resin (from Peptides International, Louisville, Ky.), polystyrene (e.g., PAM-resin available from Bachem Inc. (Torance, Calif., USA), poly (dimethylacrylamide)-grafted styrene co-divinyl-benzene (e.g., POLYHIPE® resin, available from Aminotech, Nepean, Ontario, Canada), polyamide resin (e.g. Spar-resin, available from AdvancedChemtech, Louisville, Ky., USA), polystyrene resin grafted with polyethylene glycol (available from TentaGel®, Rapp Polymere, Tubingen, Germany) polydimethylacrylamide resin (available from Milligen/Biosearch, Burlington, Mass., USA), or Sepharose (available from Pharmacia Corporation, Stockholm, Sweden).

The amino acid moiety may carry protecting groups prior to the coupling reaction. Examples of suitable protecting groups include the following: (1) acyl types such as formyl, trifluoracetyl, phthalyl, and p-toluenesulfonyl; (2) aromatic carbamate types such as benzyloxycarbonyl (Cbz or Z) and substituted benzyloxy-carbonyls, 1-(p-biphenyl)-1-methylethoxy-carbonyl, and 9-fluorenylmethyloxy-carbonyl (Fmoc); (3) aliphatic carbamate types such as tertbutyloxycarbonyl (Boc), ethoxycarbonyl, diisopropyl-methoxycarbonyl, and allyloxycarbonyl; (4) cyclic alkyl carbamate types such as cyclopentyloxycarbonyl and adamantyloxycarbonyl; (5) alkyl types such as triphenyl-methyl and benzyl; (6) trialkysilane such as trimethyl-silane; and (7) thiol containing types such as phenylthio-carbonyl and dithiasuccinoyl. The preferred protecting group is either Boc or Fmoc.

If certain functional groups or side chains on the amino acid moiety need to be protected during the coupling reaction to avoid formation of undesired bond, suitable protecting groups that can be used for that purpose are listed in Greene, *Protective Groups in Organic Chemistry*, John Wiley & Sons, New York (1981) and *The Peptides: Analysis, Synthesis, Biology*, Vol. 3, Academic Press, New York (1981), the disclosures of which are hereby incorporated by reference. Those skilled in the art will appreciate the fact that the selection and use of appropriate protecting groups depend upon the overall structure of the amino acid compound and the presence of any other protecting groups on that compound. The selection of such a protecting group may be especially important if it should not be removed during the deprotection of the other protecting group.

Suitable amino acids for the coupling reaction are listed in Table 1 along with the symbol for each amino acid.

TABLE 1

| AMINO ACID | SYMBOL |
| --- | --- |
| Alanine | Ala or A |
| Arginine | Arg or R |
| Asparagines | Asn or N |
| Aspartic acid | Asp or D |
| Cysteine | Cys or C |
| Glutamine | Gln or Q |
| Glutamic acid | Glu or E |
| Glycine | Gly or G |
| Histidine | His or H |
| Isoleucine | Ile or I |
| Leucine | Leu or L |
| Lysine | Lys or K |
| Methionine | Met or M |
| Phenylalanine | Phe or F |
| Proline | Pro or P |
| Serine | Ser or S |
| Threonine | Thr or T |
| Tryptophan | Trp or W |
| Tyrosine | Tyr or Y |
| Valine | Val or V |

More specifically, a solid phase support such as, for example, a deprotected RAM-PS resin is typically treated with 3 equivalents of the amino acid moiety and 3 equivalents of 1-hydroxybenzotriazole in a suitable organic solvent, such a N,N-dimethylformamide. Then 3 equivalents of diisopropylcarbodiimide are added and the mixture shaken for about 30 minutes to five hours. The amide that is produced can be isolated and purified by well known techniques or the crude material can be carried on to deprotection as it is.

The amide produced in the above-noted step is deprotected under conditions which do not cleave the solid phase support from the growing compound. Such conditions are well known in the art. Thus, when the Boc protecting group is used, the methods of choice are trifluoroacetic acid either neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethylformamide. When the Fmoc protecting group is used, the reagents of choice are piperidine or substituted piperidine in dimethylformamide; but any secondary amine or aqueous basic solutions can be used. The deprotection is carried out generally at a temperature of between about 0° C. and about room temperature. For example, the above-noted crude amide may be treated with 30% piperidine in N,N-dimethylformamide for about 20 minutes to about one hour, following which the reaction mixture is filtered to provide the deprotected compound.

To the deprotected compound on solid phase, a suitably amino-protected compound having free carboxylic function (for example, Fmoc-protected biphenylalanine in Scheme A) to form the solid phase linked product. For example, 1 equivalents of the deprotected compound may be combined with 3 equivalents of Fmoc-Biphenylalanine and 3 equivalents of 1-hydroxybenzo-triazole and a suitable activator (for example 3 equivalents of DIC) in a suitable organic solvent, such as N,N-dimethylformamide. The formed biphenylalanine linked compound is cleaved of the Fmoc group and then reacted with a suitable aldehyde, such as, for example, 4-phenylbenzaldehyde, to yield the corresponding Schiff base. The Schiff base is then reduced, for example, with sodium borohydride, sodium cyanoborohydride and the like, to form the corresponding amine which is then converted to the amide by reacting with, for example, an acid chloride, in this case, 4-cyanobenzoyl chloride. The amide may be converted to the thioamide which is methylated and then converted to the amidino group. The product is then cleaved of the solid phase support to yield compound 7.

The compounds of Formula II where X is an urea may be prepared as described in Scheme B:

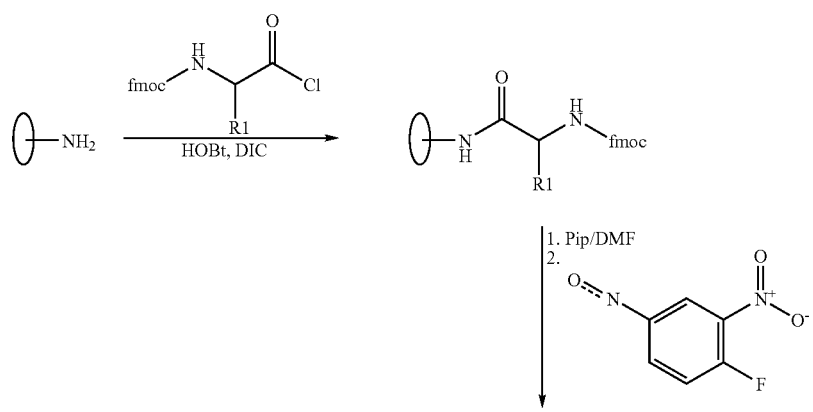

Scheme B

-continued
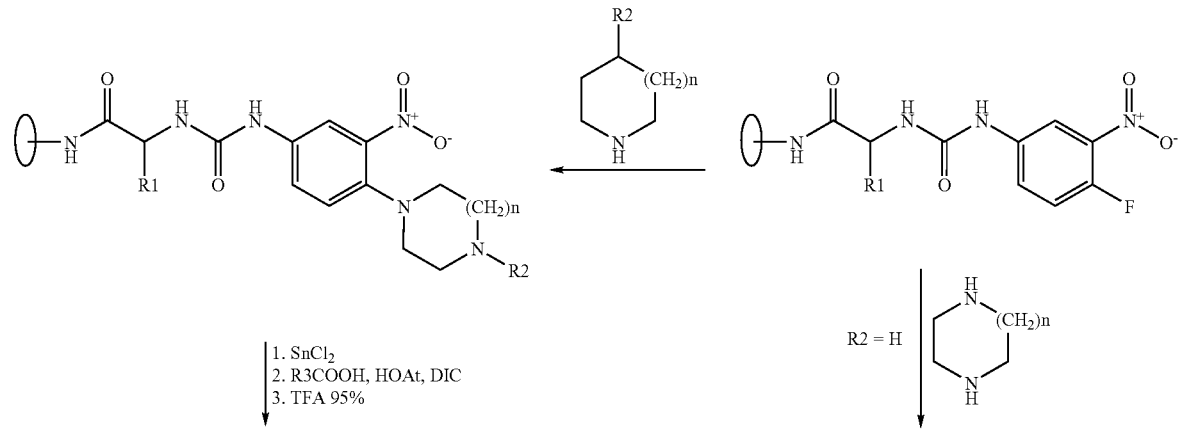
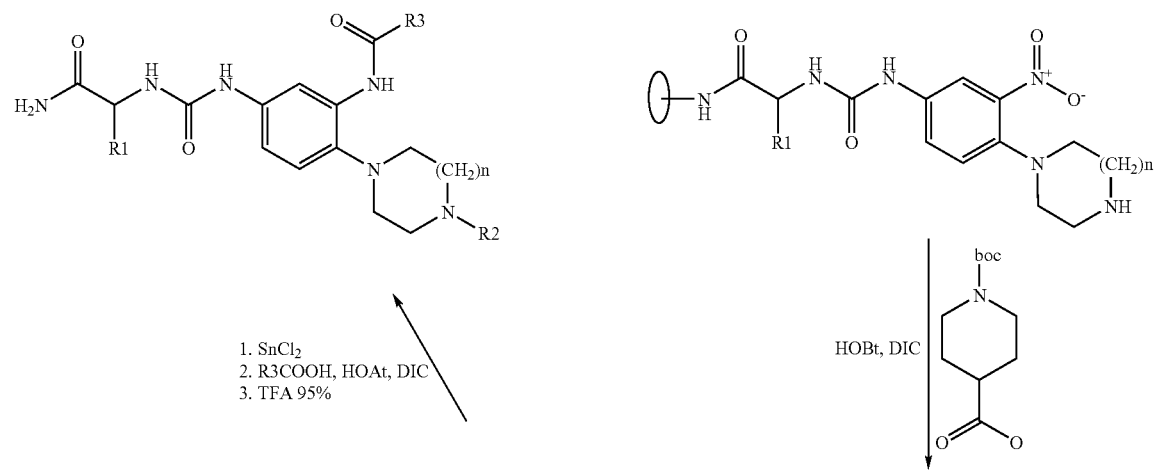
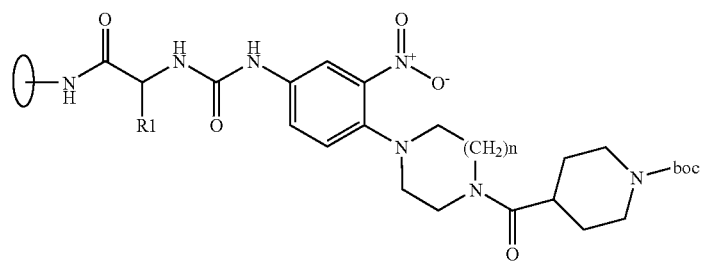

Scheme B may be explained with the synthesis of a compound of Formula II where $R_1$ is 2-naphthylmethyl, $R_2$ is cyclohexylpiperazinyl, $R_3$ is 3-phenylpropyl, X is —NH—CO—, Y is $CONH_2$ and n is 1. That compound is compound 8 identified above, 4-Cyclohexyl-1-[[2-(4-phenylbutanoyl)amino]-4-[1-aminocarbonyl-2-(2-naphthyl)ethylamino]carbonylaminophenyl]piperazine

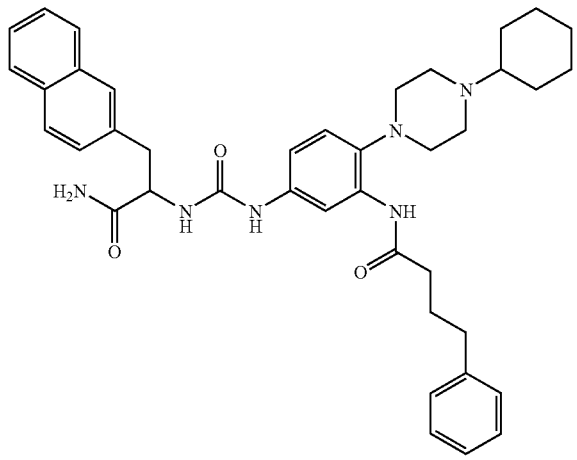

Thus, a solid phase support is coupled with a protected amino acid, in this case, Fmoc-2-naphthylalanine in the presence of an activator such as, for example, 1-hydroxybenzotriazole and DIC. It is then deprotected and then reacted with 4-fluoro-3-nitrophenylisocyanate and the fluorinated product is then reacted with 4-cyclohexylpiperazine to introduce the $R_2$ group. The nitro group is then reduced with stannous chloride to the amine which is converted to the 4-phenylbutyl amide by reacting with 4-phenylbutyric acid by activation with HOAt and DIC. Cleaving of the solid support yields the desired compound 8. Similarly, one synthesizes the other urea compounds by appropriate selection of the $R_1$, $R_2$ and $R_3$ substituted reactants.

Synthesis of a compound of Formula II where X is sulfonamide is similar to that shown in Scheme B except that in the step introducing the fluoronitrophenyl-isocyanate, the appropriate fluoronitrobenzene sulfonyl chloride is used. Thus, replacing the isocyanate in the above description with 2-fluoro-5-nitrobenzene sulfonyl chloride would yield the desired sulfonamide compound.

Isolation of the compound at various stages of the reaction scheme may be achieved after cleavage from solid support by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The thus prepared compounds may be analyzed for their composition and purity as well as characterized by standard analytical techniques such as, for example, elemental analysis, NMR, mass spectroscopy, and IR spectra.

In another embodiment, this invention provides pharmaceutical compositions comprising the above-described inventive compounds as an active ingredient. The pharmaceutical compositions generally additionally comprise a pharmaceutically acceptable carrier diluent, excipient or carrier (collectively referred to herein as carrier materials). Because of their therapeutic activity against osteoporosis and bone tissue loss, such pharmaceutical compositions possess utility in treating those diseases.

In yet another embodiment, the present invention discloses methods for preparing pharmaceutical compositions comprising the compounds of Formula I or Formula II as an active ingredient. In the pharmaceutical compositions and methods of the present invention, the active ingredient or ingredients will generally be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

The term "capsule" refers to a special container or enclosure made of methylcellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

The term "tablet" refers to a compressed or molded solid dosage form containing the active ingredients with suitable diluents. The tablet can be prepared by compression of mixtures or granulations obtained by wet granulation, dry granulation or by compaction.

The term "oral gel" refers to the active ingredients dispersed or solubilized in a hydrophilic semi-solid matrix.

The term "powders for constitution" refers to powder blends containing the active ingredients and suitable diluents which can be suspended in water or juices.

The term "diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

The term "disintegrant" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

The term "binder" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

The term "lubricant" refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

The term "glident" materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

The term "coloring agent" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

The term "bioavailability" refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, osteoporosis and bone tissue loss.

It will be apparent to those skilled in the art that many modifications, variations and alterations to the present disclosure, both to materials and methods, may be practiced. Such modifications, variations and alterations are intended to be within the spirit and scope of the present invention.

The following examples are being provided to further illustrate the present invention. They are for illustrative purposes only; the scope of the invention is not to be considered limited in any way thereby.

EXAMPLES

Unless otherwise stated, the following abbreviations have the stated meanings in the Examples below:
DCC=dicyclohexylcarbodiimide
NaBH(OAc)$_3$=sodium triacetoxyborohydride
FMOC=9-fluorenylmethyloxycarbonyl
DCE=1,2-dichloroethane
DIEA=diisopropylethylamine
Cha=cyclohexylalanine
NaI(1)=1-naphthylalanine
TEOF=triethylorthoformate
TIPS=triisopropylsilane
NaI(1)=1-naphthylalanine
Bip=4-biphenylalanine
Boc=tert.butyloxycarbonyl
Pip=piperidine
HOAc=acetic acid
TFA=trifluoroacetic acid
Py=pyridine
DIC=diisopropylcarbodiimide
MeOH=methanol
NaBH$_4$=sodium borohydride
NaBH$_3$CN=sodium cyanoborohydride
p-TsOH=p-toluenesulfonic acid
DMF: N,N-Dimethylformamide
THF: Tetrahydrofuran
DMSO: Dimethyl sulfoxide
DCM: Dichloromethane which can also be referred to as methylene chloride
LAH: Lithium aluminum hydride
HOAt: 1-Hydroxy-7-azabenzotriazole
HOBt: 1-Hydroxybenzotriazole
HRMS=High Resolution Mass Spectrometry
HPLC=High Performance Liquid Chromatography
NMR=nuclear magnetic resonance
LRMS=Low Resolution Mass Spectrometry
nM=nanomolar Additionally, "kg" refers to kilograms; "g" refers to grams; "mg" refers to milligrams; "μg" refers to micrograms; "m$^2$/g" refers to square meters per gram and is used as a measurement of particle surface area; "mmol" refers to millimoles; "L" refers to liters; "mL" refers to milliliters; "μL" refers to microliters; "cm" refers to centimeters; "M" refers to molar "mM" refers to millimolar; "μM" refers to micromolar; "nM" refers to nanomolar; "N" refers to normal; "ppm" refers to parts per million; "δ" refers to parts per million down field from tetramethylsilane; "° C." refers to degrees Celsius; "° F." refers to degrees Fahrenheit; "mm Hg" refers to millimeters of mercury; "kPa" refers to kilopascals; "psi" refers to pounds per square inch; "rpm" refers to revolutions per minute; "bp" refers to boiling point; "mp" refers to melting point; "dec" refers to decomposition; "h" refers to hours; "min" refers to minutes; "sec" refers to seconds' "R$_f$" refers to retention factor; and "R$_t$" refers to retention time.

Examples 1–7 pertain to synthesis of compounds of Formula I.

General Synthesis Procedures

Starting materials used in the synthesis were obtained from chemical vendors such as Aldrich, Sigma, Fluka, Nova Biochem and Advanced Chemtech. During the synthesis, the functional groups of the amino acid derivatives used were protected by blocking groups to prevent side reaction during the coupling steps. Examples of suitable protecting groups and their use are described in The Peptides, supra, 1981, and in vol. 9, Udenfriend and Meienhofer (eds.), 1987, which is incorporated herein by reference.

General solid-phase peptide synthesis was used to produce the compounds of the invention. Such methods are described, for example, by Steward and Young, Solid Phase Peptide Synthesis (Freeman & Co., San Francisco, 1969), which is incorporated herein by reference.

Unless indicated otherwise, peptides were synthesized on RAM™-Polystyrene Resin (Rapp Polymere, Tübingen, Germany). As an alternative to this, acid sensitive linker p-[(R, S)-α-[1-(9H-fluoren-9-yl)methoxyformamido]-2,4-dimethoxybenzyl]phenoxyacetic acid (Knorr Linker, Bernatowicz et. al, Tetr. Lett. 30 (1989) 4645, which is incorporated herein by reference) can be coupled to any amino functionalized the solid support or the desired compounds can be synthesized on polystyrene resin cross-linked with 1% divinylbenzene modified with an acid sensitive linker (Rink resin) (Rink, Tetr. Lett. 28 (1987) 3787; Sieber, Tetr. Lett. 28 (1987) 2107, each of which is incorporated herein by reference). Coupling was performed using N,N'-diisopropylcarbodiimide (DIC) in the presence of an equivalent amount of HOBt. All couplings were done N,N-dimethylformamide (DMF) at room temperature (RT). Completion of coupling was monitored by ninhydrin test. A second (double) coupling was performed where coupling in the first instance was incomplete.

Deprotection of the Fmoc group was accomplished using 50% piperidine in DMF for 2+15 min. The amount of Fmoc released was determined from the absorbance at 302 nm of the solution after deprotection, volume of washes and weight of the resin used in the synthesis.

The compound resin was at the end of the synthesis washed successively with DMF and DCM and the peptide was then cleaved and deprotected by a mixture TFA/TIPS (99/1) for 2 hours, unless specified otherwise. The resin was washed with DCM and the DCM wash combined with the TFA releasate. The solution was evaporated, the product was redissolved in a mixture of water and acetonitrile and lyophilized.

The dried compound was subjected to HPLC purification using an appropriate gradient of 0.1% TFA in water and acetonitrile (ACN). After collecting the peak containing the intended synthetic product, the solution was lyophilized and the compound was subjected to an identification process, which included electrospray mass spectrum (MS) and/or NMR to confirm that the correct compound was synthesized.

For HPLC analysis, a sample of the product was analyzed using Beckman HPLC system (consisting of 126 Solvent Deliver System, 166 Programmable Detector Module 507e Autosampler, controlled by Data Station with Gold Nouveau software) and YMC ODS-AM 4.6×250 mm column at 230 nm and flow rate 1 ml/min.

For product purification, a sample of crude lyophilized compound was dissolved in a mixture of 0.1% aqueous TFA containing 10% to 50% ACN. The solution of the product was usually filtered through a syringe connected to a 0.45

μm "ACRODISC" 13 CR PTFE (Gelman Sciences; Ann Arbor Mich.) filter. A proper volume of filtered compound solution was injected into a semi-preparative C18 column (YMC ODS-A column (20×250 mm), YMC, Inc., Wilmington, N.C.). The flow rate of a gradient or isocratic mixture of 0.1% TFA buffer and ACN (HPLC grade) as an eluent was maintained using a Beckman "SYSTEM GOLD" HPLC (Beckman, System Gold, Programmable Solvent Module 126 and Programmable Detector Module 166 controlled by "SYSTEM GOLD" software). Elution of the compound was monitored by UV detection at 230 nm. After identifying the peak corresponding to the compound under synthesis using MS, the compound was collected, lyophilized and biologically tested. MS was performed using a VG Platform (Fisons Instruments) instrument in ES+ mode. For NMR, typically samples were measured in DMSO-$d_6$ (Aldrich) using a Bruker Avance DPX 300 instrument.

Example 1

N-[4-Amidinobenzoyl]-N-[3-phenoxybenzyl]-3-(4-biphenyl)-alanyl-glycyl-amide

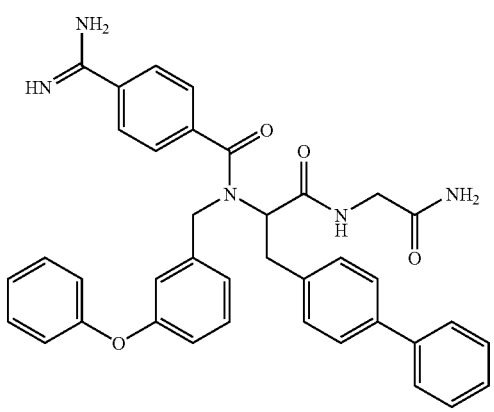

Following generally the procedure described above as Scheme A, polystyrene-RAM (substitution 0.74 mmol/g, 100–200 mesh, Rapp Polymere, Tubingen, Germany, 0.5 g) was washed with DMF and the Fmoc-protecting group cleaved by 50% solution of piperidine in DMF (twice 10 minutes, 5 ml each). The resin was then washed by DMF. Fmoc-Gly-OH (3 eq) activated with DIC/HOBt (3 eq each) in DMF (3 ml) was coupled to the resin overnight and the completion was checked by ninhydrin test. After Fmoc-group deprotection, the resin-bound intermediate was reacted with Fmoc-4-biphenyl-alanine (3 eq, in 3 ml DMF) activated with DIC/HOBt (3 eq each) overnight. Fmoc group was deprotected as described above and the resin was washed with DMF. Resin was washed with DCM and a solution of 3-phenoxybenzaldehyde (7 eq) in 5 ml TEOF/DCM (4:1) was added and the reaction was carried out for 6 hours, the resin was washed with DCM (3 times) and the formed Schiff base was reduced with 5 ml of solution NaBH$_3$CN overnight. This was prepared by mixing 1M NaBH$_3$CN in THF (commercially available) with DCE/MeOH/AcOH (80:18:2) in ratio 1:4. After the reduction resin was washed with MeOH, DMF, 10% DIEA in DMF, DMF and DCE. The resin-bound amine was reacted with 5 eq of 4-cyanobenzoyl chloride in 5 ml DCE with 5 eq DIEA overnight. Resin was then washed with DCE, DMF, with mixture pyridine/Et$_3$N (2:1) and treated with 8 ml of saturated solution of H$_2$S in Pyridine/Et$_3$N (2:1). After 5 hours, the solution was removed and the procedure repeated. After overnight standing, the resin was washed with acetone. The resulting thioamide was converted to the thioimidate by reaction with methyliodide in acetone ((4 ml of 20% solution, overnight). The resin was washed with acetone and MeOH, and a solution of 20 eq of ammonium acetate in methanol containing 20 eq of acetic acid was added and the kept at 50° C. for 3 hours. The resin was then washed with MeOH, DMF and DCM. The product was cleaved by TFA (1% TIPS). The crude product was purified by preparative HPLC. MS analysis: calculated 625.3 (M), found 626.2 (MH)+.

Example 2

Preparation of 3-amidinobenzoyl-(3-(4-tert-butylphenoxy)benzyl)-cyclohexylylalanyl-glycyl-amide

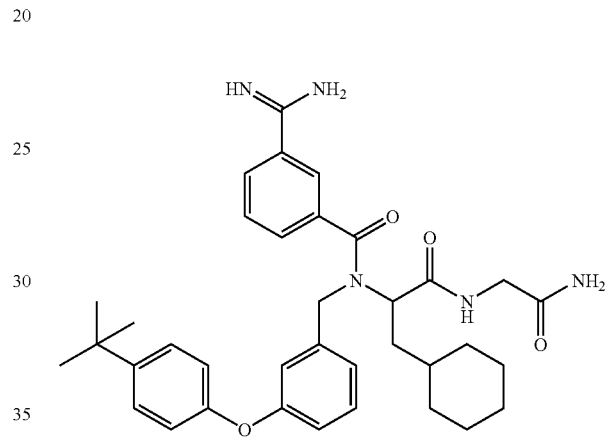

The title compound was synthesized using Fmoc-Gly-OH, Fmoc-Cha-OH, 3-(4-tert.Butylphenoxy)benzaldehyde and 3-cyanobenzoyl chloride according to procedures described in Example 1. MS analysis: calculated 611.4 (M), found 612.3 (MH)+.

Example 3

N-[3-Amidinobenzoyl]-N-[3-(4-tert-butylphenoxy)benzyl]-4-aminophenylalanyl-glycyl-amide

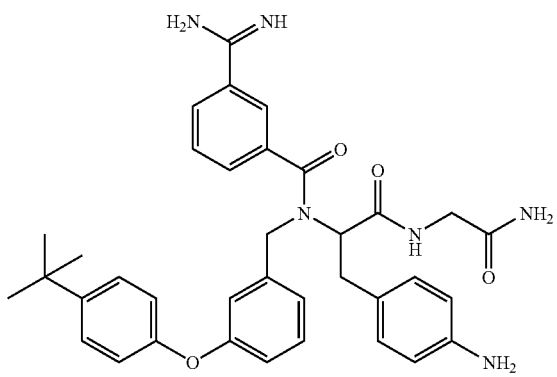

The title compound was synthesized using Fmoc-Gly-OH, Fmoc-Phe(4-NH-Boc)-OH, 3-(4-tert.Butylphenoxy)

benzaldehyde and 3-cyanobenzoyl chloride according to procedures described in Example 1. MS analysis: calculated 620.3 (M), found 621.3 (MH)+.

Example 4

N-[3-Amidinobenzoyl]-N-[3-(4-tert-butylphenoxy)benzyl]-1-naphthylalanyl-glycyl-amide

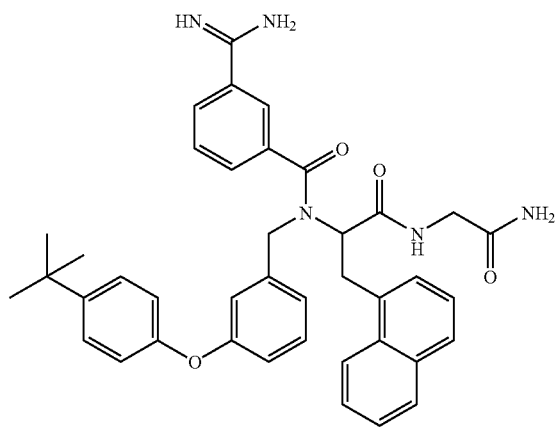

The title compound was synthesized using Fmoc-Gly-OH, Fmoc-Nal(1)-OH, 3-(4-tert.Butylphenoxy)benzaldehyde and 3-cyanobenzoyl chloride according to procedures described in Example 1. MS analysis: calculated 655.3 (M), found 656.2 (MH)+.

Example 5

N-[3-Amidinobenzoyl]-N-[3-(4-tert-butylphenoxy)benzyl]-arginyl-glycyl-amide

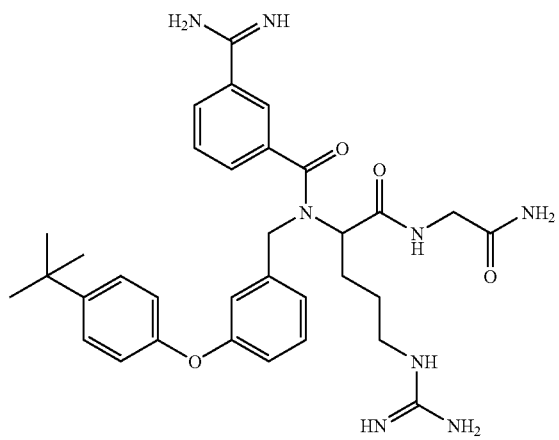

The title compound was synthesized using Fmoc-Gly-OH, Fmoc-Arg(Boc)2-OH, 3-(4-tert.Butylphenoxy)benzaldehyde and 3-cyanobenzoyl chloride according to procedures described in Example 1. MS analysis: calculated 614.3 (M), found 615.2 (MH)+.

Example 6

4-amidinobenzoyl-(3-(4-tert-butylphenoxy)phenoxybenzyl)-tryptanyl-glycyl-amide

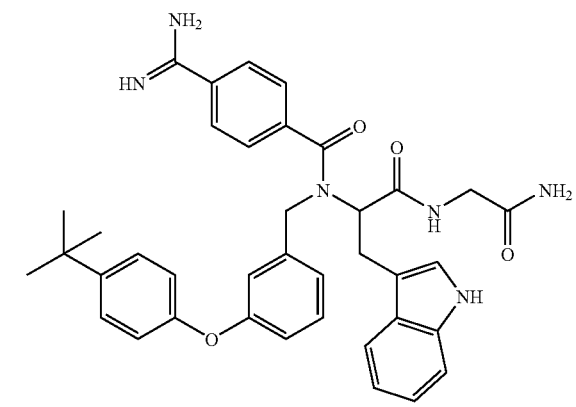

The title compound was synthesized using Fmoc-Gly-OH, Fmoc-Trp(Boc)-OH, 3-(4-tert.Butylphenoxy)benzaldehyde and 4-cyanobenzoyl chloride according to procedures described in Example 1. MS analysis: calculated 644.3 (M), found 645.2 (MH)+.

Example 7

N-[4-Amidinobenzoyl]-N-[4-biphenylmethyl]-3-(4-biphenyl)alanyl-glycyl-amide

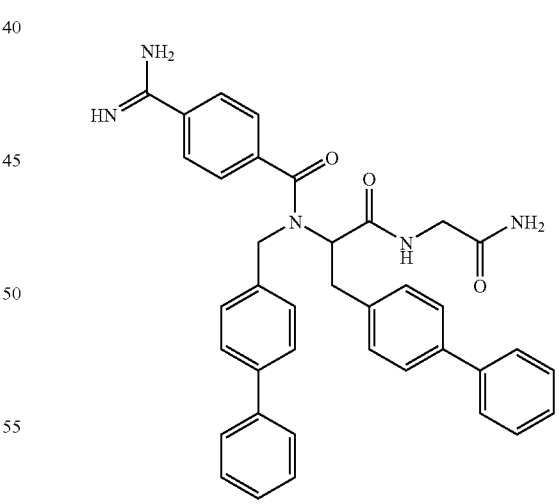

The title compound was synthesized using Fmoc-Gly-OH, Fmoc-Bip-OH, 4-phenylbenzaldehyde and 4-cyanobenzoyl chloride according to procedures described in Example 1. MS analysis: calculated 609.3 (M), found 610.2 (MH)+.

Examples 8–15 describe the synthesis of compounds of Formula II where X is a urea moiety.

Example 8

4-Cyclohexyl 1-{[2-(4-phenylbutanoyl)amino]-4-[1-aminocarbonyl-2-(2-naphthyl)ethylamino]carbonylaminophenyl}piperazine

Example 9

4-Cyclohexyl-1-{[2-cinnamoylamino]-4-[1-aminocarbonyl-2-(2-napthyl)ethylamino]carbonylaminophenyl}piperazine

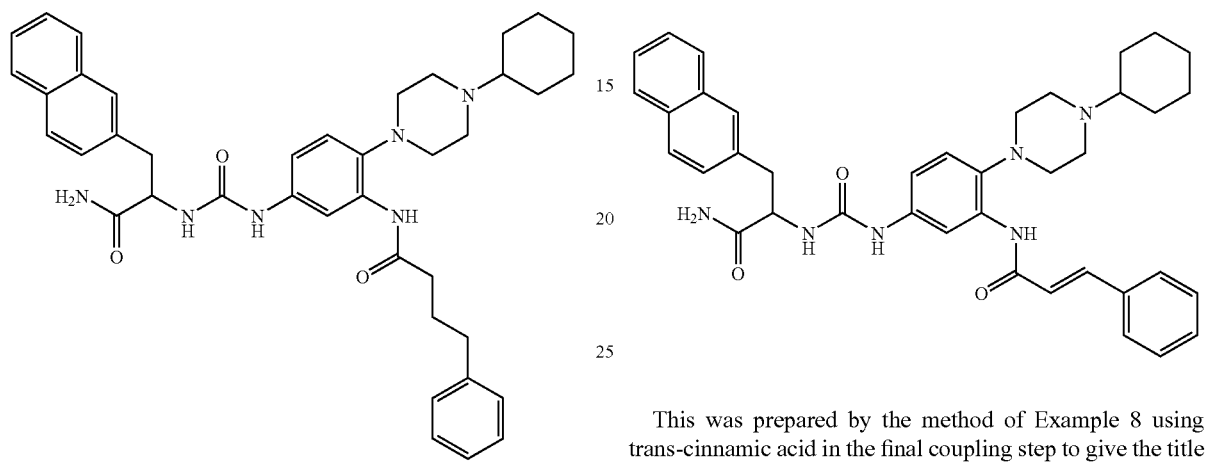

This was prepared by the method of Example 8 using trans-cinnamic acid in the final coupling step to give the title compound with M+1 ion at 645.3 and a retention time of 26.88 minutes.

Following generally the procedure described above in connection with Scheme B, commercial Polystyrene-RAM resin (0.74 mmol/g) (Rapp Polymere, Tubingen, Germany, 0.25 g) was slurried in dichloromethane, washed with DMF and treated for 30 minutes with a mixture of piperidine and DMF (1:1 v/v). The resin was washed with DMF (5×), DCM (5×) and DMF (3×) and then coupled with 0.5 mmol of Fmoc-(L)-2-naphthylalanine, 1-hydroxybenzotriazole and diisopropyl-carbodiimide in 3 ml DMF overnight. The resin was washed with DMF (5×) and treated with piperidine/DMF again for 30 minutes. After washing as described above, the coupling with 0.5 mmol of 4-fluoro-3-nitrophenylisocyanate in 2 ml DMF was carried out over night. The resin was washed with DMF (5×) and treated with 3 ml of a 0.5 molar solution of 1-cyclohexylpiperazine in DMF for 3 hours at 60°. After washing with DMF (10×), the nitro group was reduced by shaking the resin with 4 ml of a molar solution of tin chloride dihydrate in DMF for 24 hours. The resin was washed with DMF (5×), MeOH (5×), DCM (5×), DMF containing 5% of diisopropylethylamine (1×) and DMF (3×). The final coupling with 1 mmol of 4-phenyl butyric acid, 1-hydroxy-7-azabenzotriazole and diisopropylcarbodiimide in 3 ml DMF was performed over night. Following extensive washing of the resin with DMF, methanol and DCM and subsequent drying, it was cleaved with 3 ml of 95% trifluoroacetic acid. The TFA solution was evaporated and the residue was combined with the washings of the resin with methanol. Evaporation yielded the crude title compound which was purified by preparative HPLC using the standard acetonitrile/-water+0.1% TFA gradient and a Vydac C-18 column. The pure sample had a M+1 ion at 661.3 in the mass spectrum and was homogenous by HPLC with a retention time of 26.95 minutes.

Example 10

4-Cyclohexyl-1-{[2-cinnamoylamino]-4-[(1-aminocarbonyl-3-phenyl)propylamino]carbonylaminophenyl}piperazine

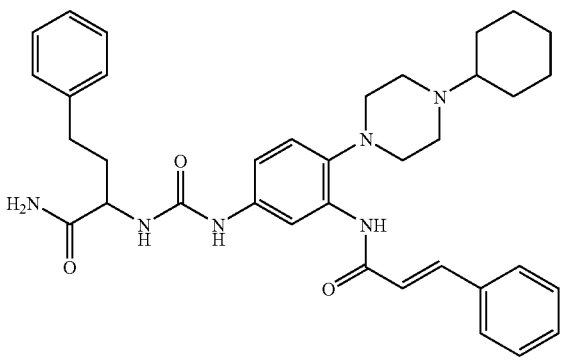

This compound was prepared by the method of Example 8 using Fmoc-homophenylalanine in the initial coupling step to give the title compound with M+1 ion at 609.3 and retention time of 25.78 minutes.

Example 11

4-Cyclohexyl-1-{[2-(4-phenylbutanoyl)amino]-4-[(1-aminocarbonyl-3-phenyl)propylamino]carbonylaminophenyl}piperazine

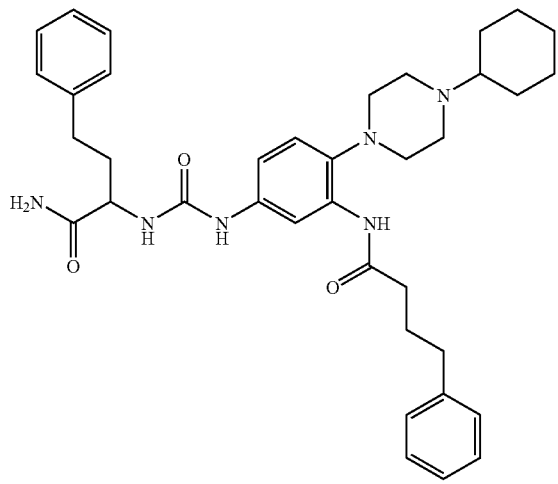

This compound was prepared by the method of Example 8 using Fmoc-homophenylalanine in the initial coupling step to give the title compound with M+1 at 625.3 and a retention time of 26 minutes.

Example 12

4-Cyclohexyl-1-{[2-cinnamoylamino]-4-[(1-aminocarbonyl-2-cyclohexyl)ethyl amino]carbonylaminophenyl}piperazine

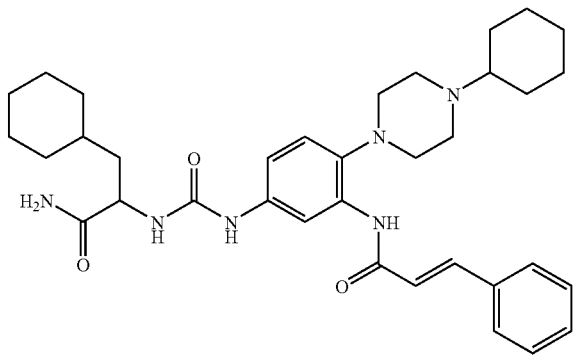

This compound was prepared by the method of Example 8 using Fmoc-cyclohexylalanine in the initial coupling step to give the title compound with M+1 ion at 601.3 and retention time of 26.72 minutes.

Example 13

4-(Piperidin-4-yl)carbonyl-1-{[2-(4-phenylbutanoyl)amino]-4-[1-aminocarbonyl-2-(2-naphthyl)ethylamino]carbonylaminophenyl}homopiperazine

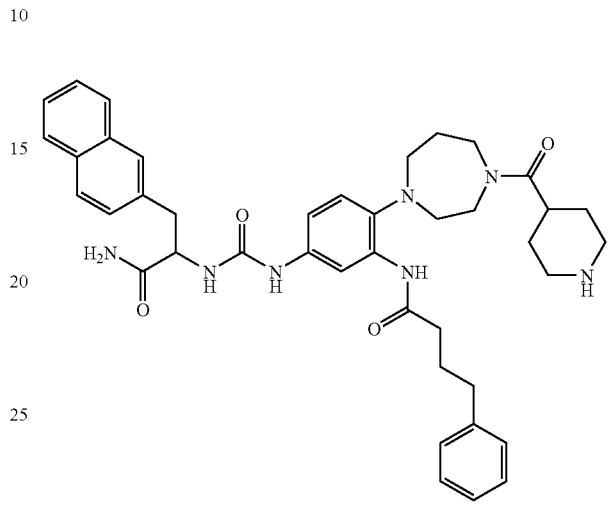

Following generally the procedure shown in Scheme B above, commercial Polystyrene-RAM resin (0.74 mmol/g) (Rapp Polymere, Tubingen, Germany, 0.25 g) was slurried in dichloromethane, washed with DMF and treated for 30 minutes with a mixture of piperidine and DMF (1:1 v/v). The resin was washed with DMF (5×), DCM (5×) and DMF (3×) and then coupled with 0.5 mmol of Fmoc-(L)-2-naphthylalanine, 1-hydroxybenzotriazole and diisopropylcarbodiimide in 3 ml DMF over night. The resin was washed with DMF (5×) and treated with piperidine/DMF again for 30 minutes. After washing as described above, the coupling with 0.5 mmol of 4-fluoro-3-nitrophenylisocyanate in 2 ml DMF was carried out over night. The resin was washed with DMF (5×) and treated with 3 ml of a 0.5 molar solution of homopiperazine in DMF for 2 hours at 60°. The resin was washed with DMF (10×) and coupled with 0.5 mmol of Boc-isonipecotic acid, HOBt and DIC in 2.5 ml of DMF over night. The resin was washed with DMF (10×) and reduced with 4 ml of a molar solution of tin chloride dihydrate in DMF for 24 hours. The resin was washed with DMF (5×), MeOH (5×), DCM (5×), DMF containing 5% of diisopropyl-ethylamine (1×) and DMF (3×). The final coupling with 1 mmol of phenylbutyric acid, 1-hydroxy-7-azabenzotriazole and diisopropylcarbodiimide in 3 ml DMF was performed over night. Following extensive washing of the resin with DMF, methanol and DCM and subsequent drying, it was cleaved with 3 ml of 95% trifluoroacetic acid. The TFA solution was evaporated and the residue was combined with the washings of the resin with methanol. Evaporation yielded the crude title compound which was purified by preparative HPLC using the standard acetonitrile/-water+0.1% TFA gradient and a Vidac C-18 column. The pure sample had a M+1 ion at 704.3 in the mass spectrum and was homogenous by HPLC with a retention time of 24.12 minutes.

Example 14

4-(Piperidin-4-yl)carbonyl-1-{[2-(2-benzofuranoyl)amino]-4-[1-aminocarbonyl-2-(2-naphthyl)ethylamino]carbonylaminophenyl}homopiperazine

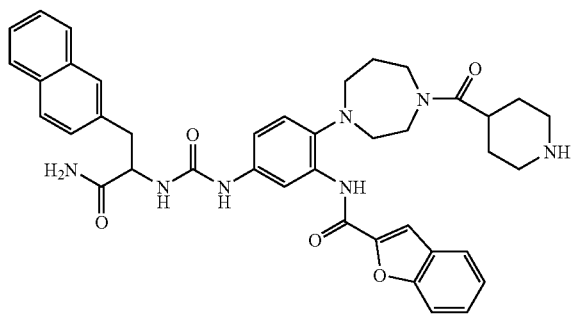

This compound was prepared by the method of Example 13 using 2-benzofuran-carboxylic acid in the final coupling step to give the title compound with M+1 ion at 702.1 and retention time of 25.5 minutes.

Example 15

4-(Piperidin-4-yl)carbonyl-1-{[2-(2-benzofuranoyl)amino]-4-[1-aminocarbonyl-2-cyclohexylethylamino]carbonylaminophenyl}homopiperazine

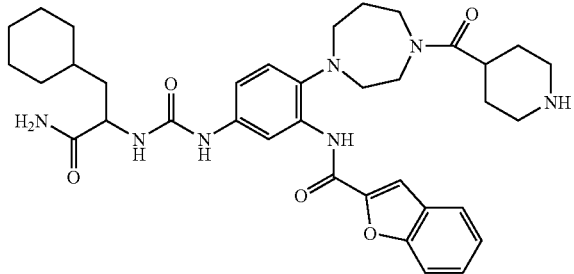

This compound was prepared by the method of Example 13 using Fmoc-cyclohexylalanine in the initial coupling step and 2-benzofurancarboxylic acid for the final acylation step to give the title compound with M+1 ion at 658.3 and retention time of 25.64 minutes.

Example 16

4-(Piperidin-4-yl)carbonyl-1-[2-[(2-benzofuranoyl)amino]-4-[[(4-aminocarbonyl)cyclohexylmethylamino]carbonylaminophenyl]-homopiperazine

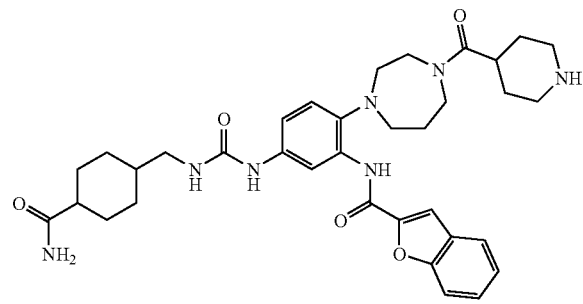

This compound was prepared by the method of Example 13 using Fmoc-trans-4-aminomethylcyclohexanecarboxylic acid in the initial coupling step and 2-benzofurancarboxylic acid for the final acylation to give the title compound with M+1 ion at 643.4 and retention time of 21.84 minutes.

Example 17

4-(Methylaminomethyl)carbonyl-1-[2-[(2-benzofuranoyl)amino]-4-[[(4-aminocarbonyl)cyclohexylmethylamino]carbonylaminophenyl]homopiperazine

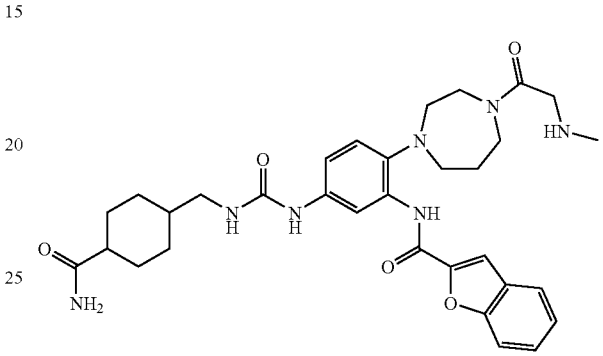

This compound was prepared by the method of Example 13 using Fmoc-trans-4-aminomethylcyclohexanecarboxylic acid in the initial coupling step and Boc-sarcosine for capping of the homopiperazine and 2-benzofurancarboxylic acid for the final acylation to give the title compound with M+1 ion at 603.3 and retention time of 21.35 minutes.

Example 18

4-(Pyrrolidin-2-yl)carbonyl-1-[2-[(2-benzofuranoyl)amino]-4-[[(4-aminocarbonyl)cyclohexylmethylamino]carbonylamino]phenyl]homopiperazine

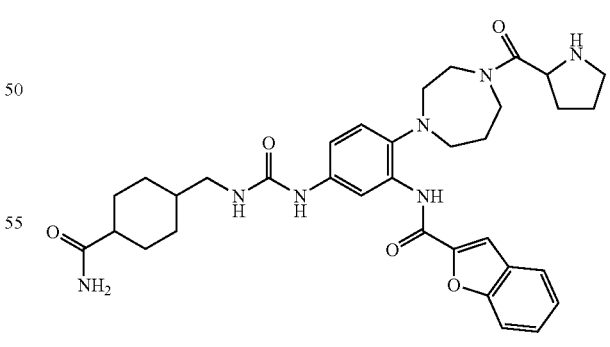

This compound was prepared by the method of Example 13 using Fmoc-trans-4-aminomethylcyclohexanecarboxylic acid in the initial coupling step, Boc-proline for capping of the homopiperazine and 2-benzofurancarboxylic acid for the final acylation to give the title compound with M+1 ion at 629.3 and retention time of 22.12 minutes.

Example 19

4-(Piperidin-1-yl)-1-[2-[(2-benzofuranoyl)amino]-4-[[(4-amino-carbonyl)cyclohexylmethylamino]carbonylaminophenyl]-piperidine

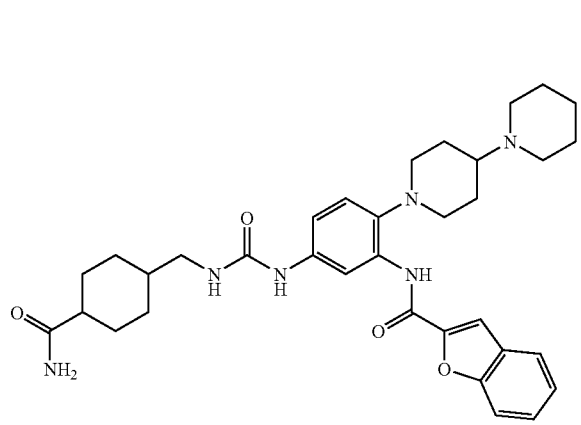

This compound was prepared by the method of Example 13 using Fmoc-trans-4-aminomethylcyclohexanecarboxylic acid in the initial coupling step, 4-(1-piperidyl)piperidine to displace the fluorine and 2-benzofurancarboxylic acid for the final acylation to give the title compound with M+1 ion at 600.3 and retention time of 22.5 minutes.

Example 20

4-(Piperidin-4-yl)carbonyl-1-[[2-(4-phenylbutanoyl)amino]-4-[1-aminocarbonyl-2-cyclohexylethylamino]carbonylaminophenyl]homopiperazine

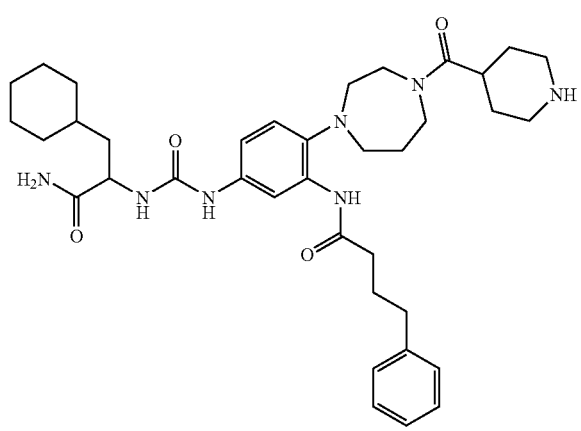

This compound was prepared by the method of Example 13 using Fmoc-L-cyclohexylalanine in the initial coupling step and Boc-isonipecotic acid for capping of the homopiperazine to give the title compound with M+1 ion at 659.4 and retention time of 23.97 minutes.

Example 21

[4-(Piperidin-4-yl)carbonyl-1-[[2-(4-phenylbutanoyl)amino]-4-[(1-aminocarbonyl-2-(naphth-2-yl))ethylamino]-carbonylaminophenyl]homopiperazine

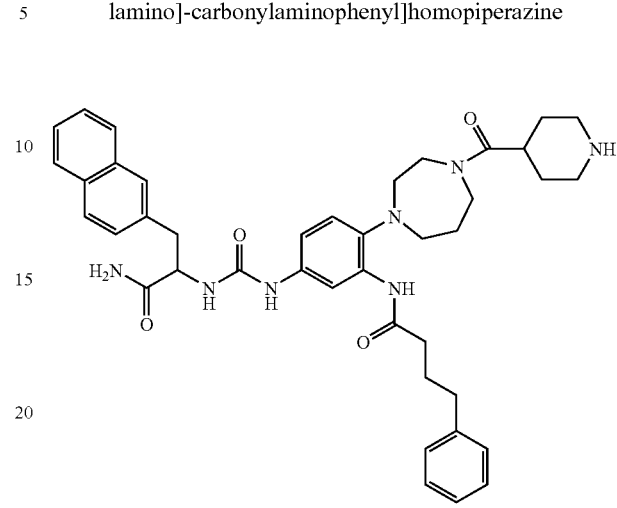

This compound was prepared by the method of Example 13 using Fmoc-homophenylalanine in the initial coupling step to give the title compound with M+1 ion at 668.4 and retention time of 22.88 minutes.

Examples 22–25 describe the synthesis of sulfonamide compounds in accordance with the compounds of the present invention.

Example 22

N-(1-Aminocarbonyl-2-methylpropyl)-2-[(4-phenylmethyl)piperidin-1-yl]-5-[(2-pyrrolidinocarbonyl)amino]phenylsulfonamide

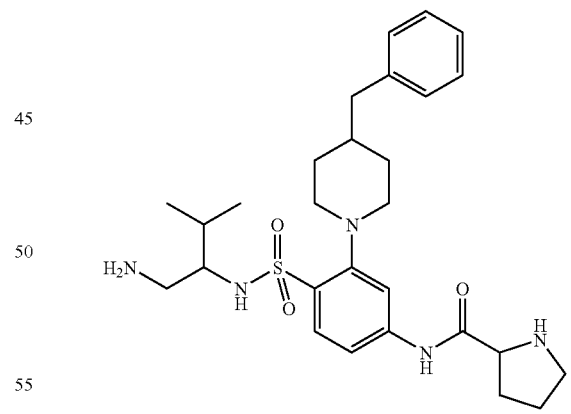

Following generally the procedures described above, commercial Polystyrene-RAM resin (0.74 mmol/g) (Rapp Polymere, Tubingen, Germany, 0.25 g) was slurried in dichloromethane, washed with DMF and treated for 30 minutes with a mixture of piperidine and DMF (1:1 v/v). The resin was washed with DMF (5×), DCM (5×) and DMF (3×) and then coupled with 0.5 mmol of Fmoc-(L)-valine, 1-hydroxybenzotriazole and diisopropylcarbodiimide in 3 ml DMF over night. The resin was washed with DMF (5×) and treated with piperidine/DMF again for 30 minutes. After washing with DMF (5×) and DCM (10×), the coupling with 0.5 mmol of 2-fluoro-5-nitrophenylsulfonyl chloride in 2 ml DCM and 1 mmol of lutidine was carried out over night. The resin was washed with DCM (5×) and DMF (5×) and treated with 3 ml of a 0.5 molar solution of 4-benzyl-piperidine in DMF for 24 hours at room temperature. After washing with DMF (10×), the nitro group was reduced by shaking the resin with 4 ml of a 0.5 molar solution of tin chloride in DMF/acetic acid 1:1 for 72 hours. The resin was washed with DMF (5×), MeOH (5×), DCM (5×), DMF containing 5% of diisopropylethylamine (1×) and DMF (3×). The final coupling with 1 mmol of 2-pyrolidinecarboxylic acid, 1-hydroxy-7-azabenzotriazole and diisopropylcarbodiimide in 3 ml DMF was performed over night. Following extensive washing of the resin with DMF, methanol and DCM and subsequent drying, it was cleaved with 3 ml of 95% trifluoroacetic acid. The TFA solution was evaporated and the residue was combined with the washings of the resin with methanol. Evaporation yielded the crude title compound which was purified by preparative HPLC using the standard acetonitrile/water+0.1% TFA gradient and a Vydac C-18 column. The pure sample had a M+1 ion at 542.3 in the mass spectrum and was homogenous by HPLC with a retention time of 26.7 minutes.

Example 23

N-(1-Aminocarbonyl-2-methylpropyl)-2-[(4-phenylmethyl)piperidin-1-yl]-5-[(4-piperdinocarbonyl)amino]phenylsulfonamide

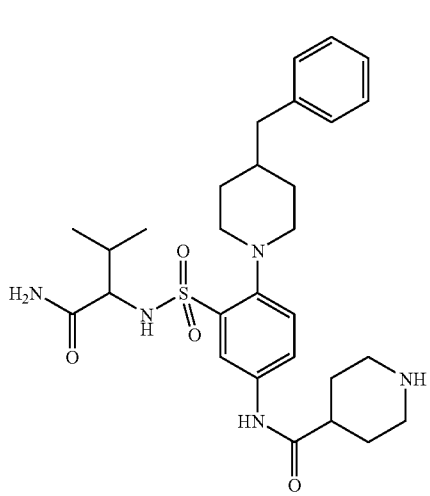

This compound was prepared by the method of Example 22 using 4-piperidinecarboxylic acid in the final coupling step to give the title compound with a M+1 ion at 556.3 in the mass spectrum and a HPLC retention time of 26.2 minutes.

Example 24

1-[2-[N-(2-Aminocarbonyl-3-methylbutyl)sulfonamido]-5-[2-cinnamoylaminol]]phenyl-4-cyclohexylpiperazine

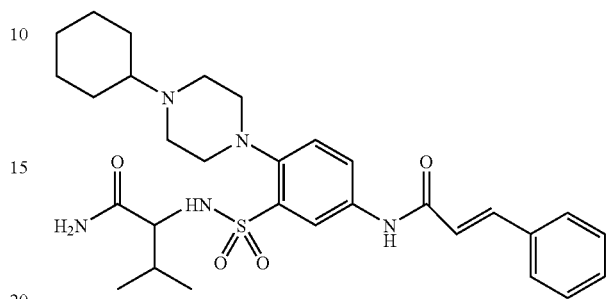

This compound was prepared by the method of Example 22 using 1-cyclohexylpiperazine for displacement of the fluorine and cinnamic acid for the final acylation step to give the title compound with a M+1 ion at 568.3 in the mass spectrum and a HPLC retention time of 24.63 minutes.

Example 25

N-[[(4-Aminocarbonyl)cyclohexylmethyl]amino]-[2-[(4-phenylmethyl)piperidin-1-yl]-5-[(2-pyrrolidinocarbonyl)-amino]phenyl]sulfonamide

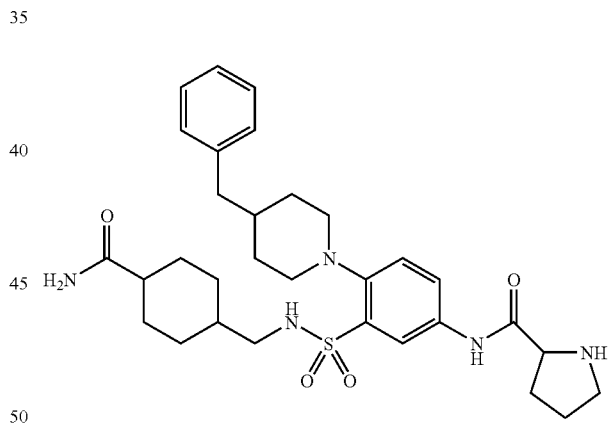

This compound was prepared by the method of Example 22 using Fmoc protected trans-4-aminomethylcyclohexanecarboxylic acid for the first coupling reaction to give the title compound with a M+1 ion at 582.3 in the mass spectrum and a HPLC retention time of 25.31 minutes.

Protein Tyrosine Kinase Activity

The compounds 1–25 above were assayed for activity with respect to the Src protein tyrosine kinase by the fluorometric method described in *Measurement of the Protein Tyrosine Kinase Activity of c-Src Using Time-Resolved Fluorometry of Europium Chelates*, Braunwalder, A. F. et al., *Analytical Biochemistry* 238, 159–164 (1996), the disclosure of which is incorporated herein by reference, using the materials and procedures further specified below.

General Assay Method for Src-Kinase:

Materials:
Costar 384 Clear, non-treated, high-binding plates
Sigma poly(Glu, Tyr) 4:1, ave. MW 35,000
Src Kinase (p60$^{C\text{-}Src}$)
Sigma ATP (1.5 mM Stock Soln. in $H_2O$)
MES Buffer: 30 mM MES (pH 6.8)
10 mM $MgCl_2$
MBI Buffer: (MES+0.4 mg/ml BSA+0.003% IGEPAL)
Wallac Eu-labelled anti-phosphotyrosine Antibody (CR04–100)
Coating Solution:
22.5 mM $Na_2CO_3$ (pH 9.6)
27.5 mM $NaHCO_3$
0.9% NaCl
Antibody Dilution Buffer: (MES+3% BSA)
DELFIA® Wash Solution (TTBS):
0.5 M NaCl
20 mM Tris (pH7.4)
0.15% Tween 20
DELFIA Enhancement Solution Method:
The plates were coated with 0.1 mg/ml poly(Glu, Tyr) in Coating Solution, 35 μl/well. It was let stand overnight at room temp. The plates were then washed 3 times with MES (100 μl/wash).

Kinase Reaction Conditions:

Procedure (Listed in Order of Addition):
  10 μl 200 μM A TP
  80 nl 5 mM test compound in DMSO
  10 μl 1:400 Src dilution in MBI Final Reaction Conditions:
  1:8000 Src Kinase
  20 μM library compound (0.4% DMSO)
  100 μM ATP
  20 μL assay volume
  15 min. at room temp.

The reaction was stopped by aspiration, and then washed 3 times with MES (100 μl/wash). 20 μl 0.4 ng/μl of antibody in Antibody Dilution Buffer (final=8ng Ab/well) was added and then incubated for 30 min. at RT. The antibody solution was removed by aspiration and then washed 3 times with 1× DELFIA Wash Solution. 20 μl DELFIA enhancement solution was added and the plates were read on a Wallac Victor plate reader in time-resolved fluorescence mode using 340 nm excitation and 615 nm emission wavelengths.

The Src Kinase inhibitory activity of the compounds, given as IC50s (μM), are listed in Table 2.

TABLE 2

| Compound No. | Activity (μMol, Delfia assay. IC50) |
|---|---|
| Example 1 | 22 |
| Example 2 | 23 |
| Example 3 | 45 |
| Example 4 | 18 |
| Example 5 | 12.5 |
| Example 6 | 14 |
| Example 7 | 13 |
| Example 8 | 8.5 |
| Example 9 | 17 |
| Example 10 | 15.5 |
| Example 11 | 11 |
| Example 12 | 18.5 |
| Example 13 | 13 |

TABLE 2-continued

| Compound No. | Activity (μMol, Delfia assay. IC50) |
|---|---|
| Example 14 | 2.75 |
| Example 15 | 6.5 |
| Example 16 | 36 |
| Example 17 | 37 |
| Example 18 | 19 |
| Example 19 | 22 |
| Example 20 | 28 |
| Example 21 | 22 |
| Example 22 | 14 |
| Example 23 | 12 |
| Example 24 | 42 |
| Example 25 | 27.5 |

From these test results and the knowledge about the compounds described in the references in the section "Background of the Invention", it would be apparent to the skilled artisan that the compounds of the invention have utility in treating conditions where selective inhibitory activity of an Src kinase is desirable. While the invention has been described in detail, modifications to illustrated embodiments within the spirit and scope of the present invention, set forth in the appended claims, will be readily apparent to those of skill in the art.

What is claimed is:

1. A compound, including pharmaceutically acceptable salts or solvates of said compound, said compound having the general structure shown in Formula II:

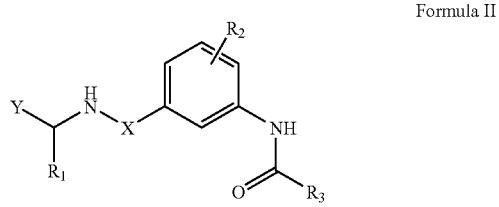

Formula II wherein $R_1$ is selected from the group consisting of H, straight chain $C_1$–$C_6$ alkyl; branched $C_1$–$C_6$ alkyl; —$(CH_2)_p$—$Ar_1$; and —$(CH_2)_p$—$R_4$, wherein p is 1 or 2;

$Ar_1$ is phenyl or naphthyl optionally substituted with a straight chain or branched $C^1$-$C^6$ alkyl group; and $R_4$ is $C_5$–$C_7$ cycloalkyl;

$R_2$ is selected from the group consisting of:

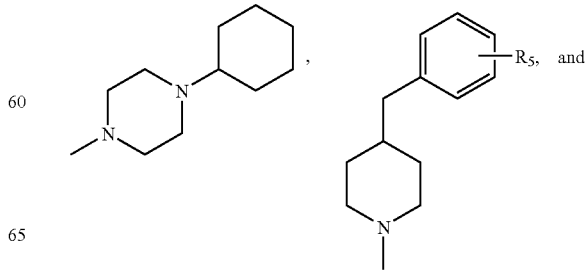

-continued

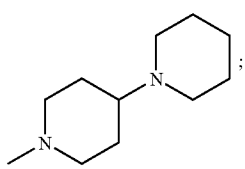

$R_5$ is selected from the group consisting of H, straight chain $C_1$–$C_6$ alkyl; branched $C_1$–$C_6$ alkyl;

$R_3$ is —$(CH_2)_q$—$Ar_2$ or —(CH═CH)-Phenyl, wherein q is an integer from 0 to 4; and $Ar_2$ is selected from the group consisting of:

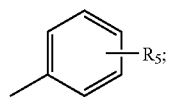

X is:

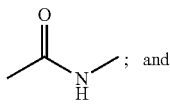

Y is selected from the group consisting of:

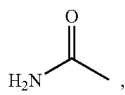 , 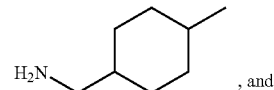 , and

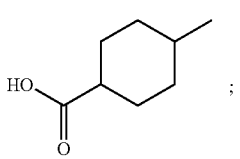 ;

with the proviso that when Y is any of the moieties:

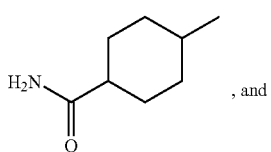 , and

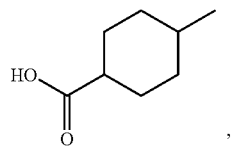 , then $R_1$ is H.

2. The compound of claim 1, wherein X is:

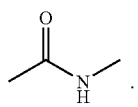 .

3. The compound of claim 1, wherein $R_1$ is H.

4. The compound of claim 1, wherein $R_1$ is a straight chain $C_1$–$C_6$ alkyl or a branched $C_1$–$C_6$ alkyl.

5. The compound of claim 1, wherein $R_1$ is —$(CH_2)_p$—$Ar_1$, where p and $Ar_1$ are as defined in claim 1.

6. The compound of claim 1, wherein $R_1$ is —$(CH_2)_p$—$R_4$, where p and $R_4$ are as defined in claim 1.

7. The compound of claim 1, wherein $R_2$ is:

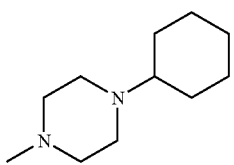 .

8. The compound of claim 1, wherein $R_2$ is:

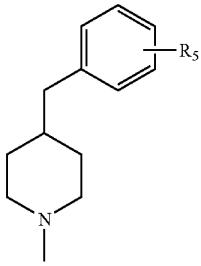

where $R_5$ is as defined in claim 1.

9. The compound of claim 1, wherein $R_2$ is:

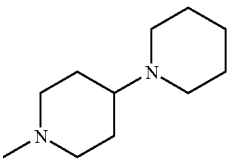 .

10. The compound of claim 1, wherein $R_3$ is —$(CH_2)_q$—$Ar_2$, where q and $Ar_2$ are as defined in claim 1.

11. The compound of claim 1, wherein $R_3$ is —(CH═CH)-Phenyl.

12. The compound of claim 1, wherein Y is:
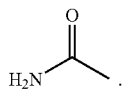
13. The compound of claim 1, wherein Y is:
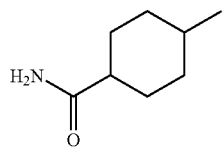
14. The compound of claim 1, wherein Y is:
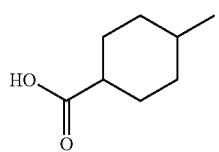
15. The compound of claim 1, wherein $R_1$ is isopropyl or isobutyl.
16. A pharmaceutical composition comprising as an active ingredient a compound of claim 1.
* * * * *